(12) United States Patent
Porges

(10) Patent No.: US 11,559,656 B2
(45) Date of Patent: *Jan. 24, 2023

(54) METHODS AND SYSTEMS FOR REDUCING SOUND SENSITIVITIES AND IMPROVING AUDITORY PROCESSING, BEHAVIORAL STATE REGULATION AND SOCIAL ENGAGEMENT BEHAVIORS

(71) Applicant: Polyvagal Science LLC, Atlantic Beach, FL (US)

(72) Inventor: Stephen Porges, Atlantic Beach, FL (US)

(73) Assignee: Polyvagal Science LLC, Atlantic Beach, FL (US)

( * ) Notice: Subject to any disclaimer, the term of this patent is extended or adjusted under 35 U.S.C. 154(b) by 376 days.

This patent is subject to a terminal disclaimer.

(21) Appl. No.: 16/846,599

(22) Filed: Apr. 13, 2020

(65) Prior Publication Data

US 2020/0238046 A1 Jul. 30, 2020

Related U.S. Application Data

(63) Continuation of application No. 16/018,282, filed on Jun. 26, 2018, now Pat. No. 10,661,046, which is a
(Continued)

(51) Int. Cl.
*A61B 5/12* (2006.01)
*A61M 21/00* (2006.01)
*A61B 5/00* (2006.01)

(52) U.S. Cl.
CPC ............... *A61M 21/00* (2013.01); *A61B 5/12* (2013.01); *A61B 5/125* (2013.01); *A61B 5/486* (2013.01);
(Continued)

(58) Field of Classification Search
CPC .......... A61M 21/00; A61B 5/12; A61B 5/121; A61B 5/123; A61B 5/125; A61B 5/128; A61B 5/486
See application file for complete search history.

(56) References Cited

U.S. PATENT DOCUMENTS

| 6,986,747 B2 | 1/2006 | McCulloch et al. |
| 7,231,240 B2 | 6/2007 | Eda et al. |
(Continued)

FOREIGN PATENT DOCUMENTS

WO 2016100195 A1 6/2016

OTHER PUBLICATIONS

Extended European Search Report issued for EP Patent App. 19760768.2, dated Apr. 1, 2021, 16 pp.
(Continued)

*Primary Examiner* — John P Lacyk
(74) *Attorney, Agent, or Firm* — MG Miller Intellectual Property Law LLC

(57) ABSTRACT

Various embodiments are described herein to reduce sound sensitivities, improve state regulation, and/or reduce auditory processing and social engagement deficits in individuals with such deficiencies by recruiting the anti-masking functions of the middle ear muscles in order to optimize the transfer function of the middle ear for the processing of human speech. In certain embodiments, an individual may be subjected to a training protocol comprising one or more training sessions. During each training session, acoustic stimuli are provided to a subject for a period of time, with or without accompanying visual stimulation. A user response may be determined, for example, before beginning the protocol, during a session, after a session, and/or upon completion of the protocol. Such user response may be employed to adjust the acoustic stimulation, and the adjusted
(Continued)

acoustic stimulation may be provided to the subject during a subsequent training session (or at a subsequent time within the same training session). The training protocol may end after a predetermined number of training sessions or upon achieving a desired user response. The training session may be characterized by a fixed protocol during which continuous stimulation is presented for a fixed period of time or by an interactive protocol during which the stimulation presentation is dependent on the reactions of the subject.

19 Claims, 10 Drawing Sheets

Related U.S. Application Data continuation of application No. 15/799,140, filed on Oct. 31, 2017, now Pat. No. 10,029,068.

(60) Provisional application No. 62/415,996, filed on Nov. 1, 2016.

(52) U.S. Cl.
CPC ............... *A61M 2021/0027* (2013.01); *A61M 2205/3303* (2013.01); *A61M 2205/3331* (2013.01); *A61M 2205/3375* (2013.01); *A61M 2205/3553* (2013.01); *A61M 2205/50* (2013.01); *A61M 2205/581* (2013.01); *A61M 2205/582* (2013.01); *A61M 2205/583* (2013.01); *A61M 2230/04* (2013.01)

(56) References Cited

U.S. PATENT DOCUMENTS

| | | | |
|---|---|---|---|
| 10,029,068 B2 * | 7/2018 | Porges | A61M 21/00 |
| 10,426,956 B2 | 10/2019 | Williamson et al. | |
| 10,661,046 B2 * | 5/2020 | Porges | A61M 21/00 |
| 2006/0122675 A1 | 6/2006 | Libbus et al. | |
| 2006/0122676 A1 | 6/2006 | Ko et al. | |
| 2006/0253161 A1 | 11/2006 | Libbus et al. | |
| 2008/0147138 A1 | 6/2008 | Maskara et al. | |
| 2008/0249439 A1 | 10/2008 | Tracey et al. | |
| 2008/0319513 A1 | 12/2008 | Pu et al. | |
| 2009/0187230 A1 | 7/2009 | DiLorenzo | |
| 2009/0234406 A1 | 9/2009 | Shuros et al. | |
| 2012/0277521 A1 | 11/2012 | Chamberlin | |
| 2013/0009993 A1 | 1/2013 | Horseman | |
| 2013/0066395 A1 | 3/2013 | Simon et al. | |
| 2013/0211471 A1 | 8/2013 | Libbus et al. | |
| 2013/0245722 A1 | 9/2013 | Ternes et al. | |
| 2014/0358193 A1 | 12/2014 | Lyons et al. | |
| 2015/0306395 A1 | 10/2015 | Libbus et al. | |
| 2016/0066847 A1 | 3/2016 | Sales et al. | |
| 2016/0354543 A1 | 12/2016 | Cinar et al. | |
| 2017/0120052 A9 | 5/2017 | Simon et al. | |

OTHER PUBLICATIONS

Patriquin et al., Respiratory sinus arrhythmia: A marker for positive social functioning and receptive language skills in children with autism sprectrum disorders, Developmental Psychobiology, Mar. 1, 2013, vol. 55, No. 2, pp. 101-112.

Sullivan et al., Yoga Therapy and Polyvagal Theory: The Convergence of Traditional Wisdom and Contemporary Neuroscience for Self-Regulation and Resilience, Frontiers in Human Neuroscience, Feb. 27, 2018, vol. 12.

Denver, John et al., Methodological issues in the quantification of respiratory sinus arrhythmia, Biological Psychology, Oct. 25, 2006, 286-294, Elsevier B.V.

Lewis, Gregory F. et al., Statistical strategies to quantify respiratory sinus arrhythmia: Are commonly used metrics equivalent?, Biological Psychology, De. 3, 2011, pp. 349-364, vol. 89, SciVerse ScienceDirect.

* cited by examiner

METHODS AND SYSTEMS FOR REDUCING SOUND SENSITIVITIES AND IMPROVING AUDITORY PROCESSING, BEHAVIORAL STATE REGULATION AND SOCIAL ENGAGEMENT BEHAVIORS

CROSS-REFERENCE TO RELATED APPLICATIONS

The present application is a continuation of U.S. utility patent application Ser. No. 16/018,282, titled "Methods and Systems For Reducing Sound Sensitivities and Improving Auditory Processing, Behavioral State Regulation and Social Engagement Behaviors," filed Jun. 26, 2018, which is a continuation of U.S. utility patent application Ser. No. 15/799,140, titled "Methods and Systems For Reducing Sound Sensitivities and Improving Auditory Processing, Behavioral State Regulation and Social Engagement Behaviors," filed Oct. 31, 2017, which claims the benefit of U.S. provisional patent application Ser. No. 62/415,996, titled "Methods and Systems For Reducing Sound Sensitivities and Improving Auditory Processing, Behavioral State Regulation and Social Engagement Behaviors," filed Nov. 1, 2016. Each of the above applications is incorporated by reference herein in its entirety.

BACKGROUND

This specification relates generally to acoustic therapies for the treatment of various conditions, such as sound sensitivities, behavioral and autonomic state regulation difficulties, atypical social engagement behaviors and/or auditory processing deficits.

Sound sensitivities, difficulties in behavioral and autonomic state regulation, atypical social engagement behaviors and auditory processing deficits are prevalent symptoms in autism spectrum disorders ("ASD") and other psychiatric diagnoses, such as Post-traumatic stress disorder ("PTSD"). These symptoms may also be present in individuals with developmental disabilities (e.g., Fragile X Syndrome, Prader Willi Syndrome), as well as in aging individuals and those who have been subjected to abuse or neglect.

Sound sensitivities may be experienced as a discomfort with background ambient sounds or a sensitivity to specific sounds. Such symptoms may be dependent or independent of sound source or the specific frequencies and/or loudness of sound. Problems in state regulation may be expressed as atypical autonomic regulation, atypical social and emotional behaviors, low reactivity thresholds, chronic pain, tantrums, difficulties in sustaining attention and/or sleep disorders. And auditory processing deficits may be experienced as language and speech delays, difficulties in extracting human voice from background sounds and/or as a general compromise in social communication skills.

The mechanisms mediating sound sensitivities, autonomic and behavioral state regulation, social engagement and auditory processing are generally assumed to represent disparate response systems. From an empirical perspective, behavioral state regulation and social engagement are manifested in observable behaviors; autonomic regulation is observed in peripheral physiological reactions and medical systems; sound sensitivities are manifested through subjective experiences; and auditory processing is manifested in expressive and/or receptive language skills. Because sound sensitivities and deficits in state regulation, social engagement, and auditory processing lack diagnostic specificity, researchers who study the neurobiological and biobehavioral features of a specific psychiatric diagnosis (e.g., ASD, PTSD, etc.) or a genetic-based neurodevelopment disorder (e.g., Fragile X Syndrome, Prader Willi Syndrome, etc.) have not focused on these domains.

Moreover, sound sensitivities, behavioral and autonomic state regulation, social engagement and auditory processing are dependent on response systems that are studied by different scientific disciplines, which have little interaction and virtually no common language. For example, the study of psychiatric disorders (i.e., diagnoses), autonomic state regulation problems (e.g., symptoms manifested in visceral organs such as cardiovascular or digestive disorders), behavioral problems (e.g., state regulation and tantrums), psychological difficulties (e.g., emotional instability), sound sensitivities (e.g., a general or selective hypersensitivity to sounds), auditory processing disorders (e.g., difficulties understanding verbal instructions), and cognitive deficits (e.g., language delays) represent research domains investigated by separate disciplines. These distinctions contribute to conventional models of inquiry applied in clinical neuroscience, which rely on separate disciplines to categorize, investigate, treat, and explain the neurobiological mechanisms of clinical disorders.

One particular theory, the Polyvagal Theory, proposes a strategy that applies evolution as an organizing principle to understand a link between sound sensitivities, behavioral and autonomic state regulation, social engagement and auditory processing. According to the Polyvagal Theory, the well-documented phylogenetic shift in neural regulation of the autonomic nervous system provided mammals with a neural circuit that promotes social interactions in safe contexts by supporting calm physiological states and an ability to process relatively soft vocalizations in a frequency band distinct from the lower frequencies associated with reptilian predators. This "mammalian" circuit functions as the neural substrate for an integrated, social engagement system that dampens the functional impact of sounds outside the frequency band of vocalizations employed for social communication and regulates the neural circuits that optimize behavioral state, social engagement, and auditory processing.

An exemplary social engagement system according to the Polyvagal Theory is illustrated in FIG. 1. As shown, the social engagement system 100 includes a somatomotor component 140 with special visceral efferent pathways traveling through five cranial nerves 130 (i.e., the trigeminal nerve (V), facial nerve (VII), glossopharyngeal nerve (IX), vagus nerve (X) and accessory nerve (XI)) that regulate the striated muscles of the face and head (e.g., middle-ear muscles 141, laryngeal muscles 142, muscles of mastication 143, facial muscles 144, pharyngeal muscles 145 and head-turning muscles 146). The somatomotor component 140 regulates the pitch of vocalizations, the tension on the middle-ear muscles to enhance detection and processing of vocalizations, and facial expressions that supplement communicated messages and allow a listener to provide feedback to a vocalizer.

The social engagement system 100 also includes a visceromotor component 150 with the myelinated vagus that regulates the heart 151 and bronchi 152 to adjust an individual's physiological state to be complement their facial and vocal signals of social communication. Thus, the visceromotor component 150 allows for an individual to project a physiological state of calmness or defense through voice and face. Coincident with this projection of physiological state, the middle-ear muscles change muscle tone to either facilitate the processing of vocalizations (e.g., by dampening the transfer of acoustic energy representing low frequencies in the background) or enhance the processing of low frequency acoustic energy at the expense of dampening the ability to extract the acoustic information of vocalizations. Because, via evolution, low-frequency acoustic information signaled predator or environmental danger, this system requires cues of "safety."

Based on the Polyvagal Theory, sound sensitivities and deficits in state regulation, social engagement and auditory processing may be paralleled by reduced vagal influences to the heart and bronchi via myelinated vagal pathways. Such a reduction is an adaptive response strategy to support mobilization (i.e., so-called "fight-flight" behaviors) in dangerous environments. Since the Polyvagal Theory articulates a hierarchy of neural circuits, the metabolic resources necessary for fight-flight behaviors are not efficiently available unless there is a retraction of the vagal brake—a calming mechanism that functions via the myelinated vagus to slow heart rate, optimize oxygenation of the blood, and to downregulate the sympathetic nervous system. This neurophysiological calming mechanism downregulates defensive states and enables social engagement behaviors to spontaneously occur. Thus, the neural mechanisms defining the social engagement system provide a plausible model to explain why sound sensitivities and both auditory processing and state regulation difficulties are prevalent in individuals with ASD and other clinical disorders. Consistent with this model, features of the social engagement system become windows of assessment and, due to the integrated nature of the system, these features may also be portals for possible intervention.

One particular portal of interest lies in the neural regulation of the middle-ear muscles. These muscles facilitate the extraction of human speech by dampening the transmission of low-frequency noise from the external environment to the inner ear. Sound enters the outer ear and travels, through the external auditory canal, to the eardrum where it is transduced by the structures of the middle ear (i.e., small bones comprising the ossicular chain) that connect the eardrum with the cochlea.

The rigidity of the ossicular chain determines the stiffness of the eardrum, which, in part, determines the acoustic properties of sounds transmitted to the inner ear. The middle-ear muscles, via cranial nerves, regulate the position of the ossicles and stiffen or loosen the eardrum. When the eardrum is "tightened," higher frequencies are absorbed and transmitted to the inner ear and the energy of lower frequencies is attenuated (i.e., reflected) before being encoded by the inner ear (i.e., the cochlea) and transmitted via the auditory nerve (i.e., cranial nerve VIII) to the cortex. Complementing the ascending pathways are descending pathways that regulate the middle-ear muscles, which functionally determine the energy (i.e., attenuate, pass, or amplify) of specific frequencies that reach the inner ear.

The features describing the transformation of sound intensity from the outer ear to the inner ear defines the middle-ear transfer function. If the acoustic information in the frequency band associated with speech is distorted by an atypical middle-ear transfer function, the information coded by the inner ear (and subsequently transmitted to the cortex) may not contain sufficient information to enable accurate detection of speech sounds. In addition, there are descending pathways that regulate the hair cells in the cochlea to fine tune auditory perception, which is especially important in the development of language skills. If the acoustic information related to human speech that reaches the cortex via ascending pathways is distorted, then the descending pathways to the cochlea may also be atypical and will further distort the individual's ability to process speech and to produce language.

Atypical central regulation of peripheral middle-ear structures may pass low-frequency sounds that dominate the acoustic spectrum in our mechanized society (e.g., ventilation systems, traffic, airplanes, vacuum cleaners, and other appliances). This may result in both a hypersensitivity to sounds and a distortion or "masking" of the frequency components associated with human speech reaching the brain. Thus, an atypical middle-ear transfer function may be a potentially parsimonious explanation of both the auditory hypersensitivities and the difficulties in auditory processing frequently associated with autism.

There is a need in the art for systems and methods that can rehabilitate the integrated social engagement system via exercise of a specific portal, such as the middle-ear muscles.

SUMMARY

Various acoustic therapy systems and methods are described herein that are capable of treating various conditions, such as sound sensitivities, behavioral and autonomic state regulation difficulties, atypical social engagement behaviors and/or auditory processing deficits. Exemplary embodiments present processed acoustic stimuli to a subject in order to recruit and/or exercise neural regulation of the subject's middle-ear muscles.

It is an object of the embodiments to provide methods and systems for treating symptoms associated with aging, ASD, PTSD, and other clinical disorders, such as sound sensitivities, behavioral and autonomic state regulation deficiencies and/or auditory processing and social engagement deficits, by engaging neural regulation of specific structures described as part of the social engagement system (see FIG. 1 at 100).

It is another object of the embodiments to provide methods and systems for treating sound sensitivities, behavioral and autonomic state regulation deficiencies and/or auditory processing and social engagement deficits, the results of which may be measured through well-defined indices of auditory hypersensitivities and auditory processing, and through innovative indices of the middle-ear transfer function and/or physiological state (i.e., through measure of autonomic function).

It is another object of the embodiments to provide methods and systems for treating sound sensitivities, behavioral and autonomic state regulation deficiencies and/or auditory processing and social engagement deficits, wherein such embodiments are designed to engage and exercise the neural regulation of the middle-ear muscles, and provide an understanding of the transfer function of the middle-ear structures and the vulnerability of the fast twitch middle-ear muscles to fatigue.

It is yet another object of the embodiments to provide methods and systems for treating sound sensitivities, behavioral and autonomic state regulation deficiencies, auditory processing and social engagement deficits, chronic pain and associated conditions, anxiety disorders, blood sugar regulation deficiencies and/or conditions associated with aging, wherein a treatment protocol employs a noninvasive, acoustic vagal nerve stimulation to increase vagal activity to the heart via an auditory pathway.

In one embodiment, a method is provided wherein an acoustic input signal is processed according to processing parameters to produce acoustic stimuli during a session. The processing parameters may include a first frequency modulation cycle that includes a first initial modulation, a first widest modulation and a first final modulation. The first initial modulation may be defined by a first initial low-frequency limit of from about 600 Hz to about 900 Hz and a first initial high-frequency limit of from about 1,400 Hz to about 2,000 Hz. The first widest modulation may be defined by a first minimum low-frequency limit that is lower than the first initial low-frequency limit and a first maximum high-frequency limit that is higher than the first initial high-frequency limit. And the first final modulation may be defined by a first final low-frequency limit that is substantially similar to the first initial low-frequency limit and a first final high-frequency limit that is substantially similar to the first initial high-frequency limit.

The processing parameters may further include a second frequency modulation cycle that includes a second initial modulation, a second widest modulation and a second final modulation. The second initial modulation may be defined by a second initial low-frequency limit and a second initial high-frequency limit. The second widest modulation may be defined by a second minimum low-frequency limit that is lower than the second initial low-frequency limit and a second maximum high-frequency limit that is higher than the second initial high-frequency limit. And the second final modulation may be defined by a second final low-frequency limit that is substantially similar to the second initial low-frequency limit and a second final high-frequency limit that is substantially similar to the second initial high-frequency limit. The second minimum low-frequency limit of the second widest modulation may be lower than the first minimum low-frequency limit of the first widest modulation of the first modulation cycle. Moreover, the second maximum high-frequency limit of the second widest modulation may be higher than the first maximum high-frequency limit of the first widest modulation of the first modulation cycle. It will be appreciated that the processing parameters may include any number of modulation cycles and each modulation cycle may include any number of modulations.

The method may further include transmitting the acoustic stimuli to the subject during the session to thereby recruit one or more anti-masking functions of one or more middle-ear muscles of the subject. And the method may also include determining that the subject has experienced a user response, such as one or more of reduced sound sensitivity, improved auditory processing, improved behavioral state regulation, improved autonomic state regulation, improved middle-ear transfer function and improved social engagement.

In certain embodiments, the method may include measuring one or more characteristics of the subject before processing the acoustic input signal to acoustic stimuli, wherein the one more characteristics are selected from the group consisting of: sound sensitivity, behavioral state regulation, autonomic state regulation, auditory processing, one or more social engagement skills, sucking, swallowing, breathing, one or more acoustic properties of vocalization of the subject, heart rate variability ("HRV"), respiratory sinus arrhythmia ("RSA"), heart rate, blood pressure, cognitive ability, pain level, anxiety level, blood sugar level, usage of one or more facial muscles, usage of one or more head-turning muscles and a middle-ear transfer function. Optionally, such measurements may be employed to adjust the processing parameters.

The details of one or more embodiments of the subject matter of this specification are set forth in the accompanying drawings and the description below. Other features, aspects, and advantages of the subject matter will become apparent from the description, the drawings, and the claims.

DETAILED DESCRIPTION

Figure 1:
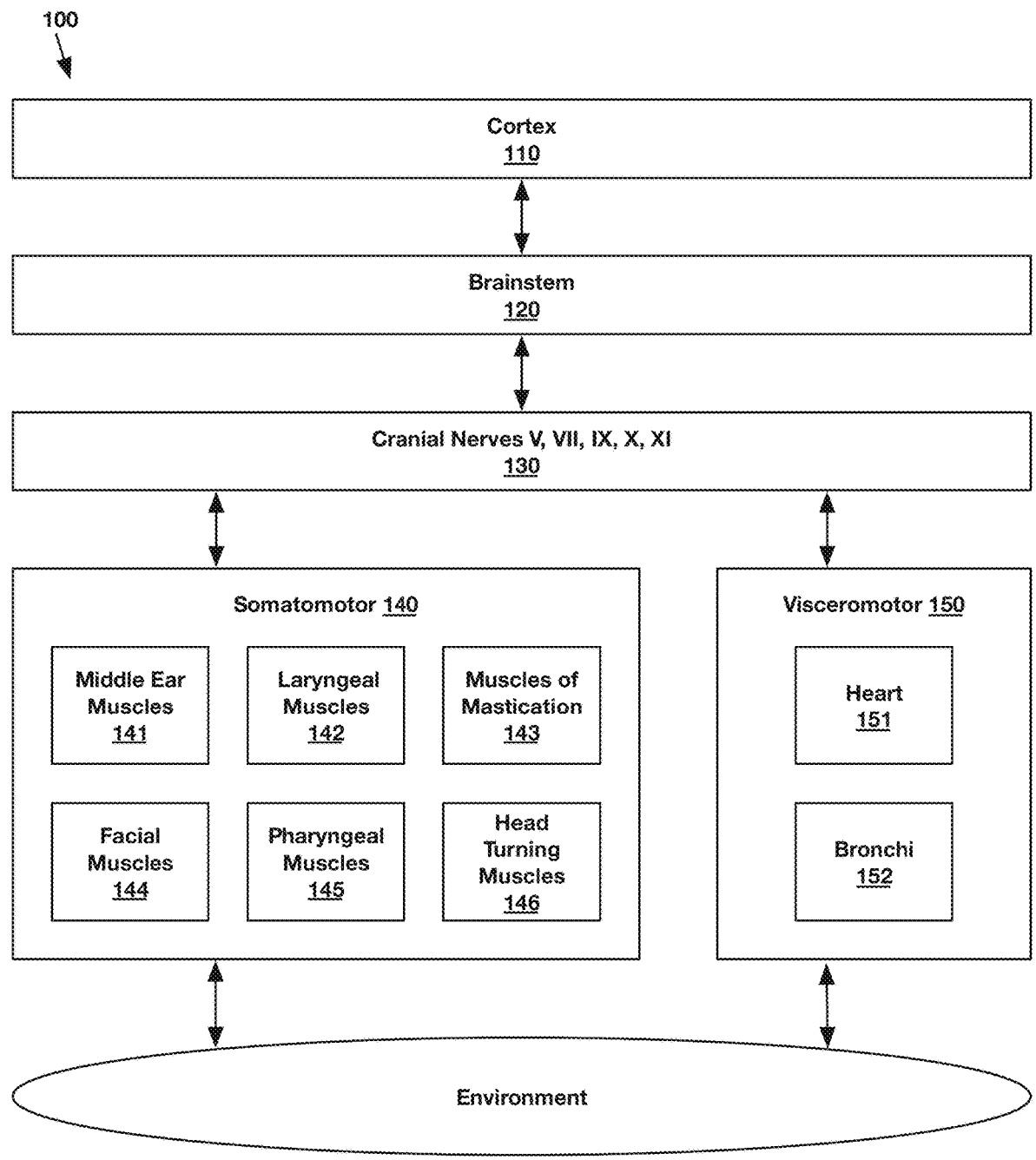
FIG. 1 shows an exemplary social engagement system 100 according to the Polyvagal Theory.

Various embodiments are described herein to reduce sound sensitivities, improve behavioral and autonomic state regulation, and/or reduce auditory processing and social engagement deficits in individuals with such deficiencies by recruiting the anti-masking functions of the middle-ear muscles in order to optimize the transfer function of the middle ear for the processing of human speech. In certain embodiments, an individual may be subjected to a training protocol comprising one or more training sessions. During each training session, modulated acoustic stimulation is provided to a subject, with or without accompanying, synchronized visual stimulation (e.g., video, virtual reality ("VR") environment, etc.). A user response may be determined, for example, before beginning the protocol, during one or more sessions, after one or more sessions and/or upon completion of the protocol. Such user response(s) may be employed to adjust one or more parameters of the protocol, including but not limited to: the total number of sessions, the length of one or more sessions and/or the acoustic stimulation provided during one or more sessions. Accordingly, each training session may comprise a predetermined period of time or a variable period of time based on user response. Similarly, the training protocol may end after a predetermined number of sessions or upon achieving a desired user response.

It has surprisingly been found that the exemplary methods and systems described herein may enhance the function of the social engagement system described by the Polyvagal Theory 100, leading to improved auditory processing, reduced auditory hypersensitivities, changes in autonomic state characterized by increased vagal regulation of the heart (e.g., increases in HRV and RSA), and increased spontaneous social behaviors (e.g., sharing).

Without wishing to be bound to a particular theory, it is believed that the specific acoustic stimuli provided to a subject during training exercises the neural regulation of the middle-ear muscles. By modulating the frequency band associated with human vocalizations, the ascending pathways provide dynamically changing information that feeds back on the descending pathways regulating the middle-ear muscles. Metaphorically, exemplary methods described herein may be conceptualized as a "treadmill" exercise for the middle-ear muscles, where such muscles are engaged to listen and process features of dynamically changing acoustic stimuli. Accordingly, the exemplary methods may be employed to "rehabilitate" acoustic reflex functionality of the middle-ear muscles and/or to normalize the middle-ear transfer function.

It is believed the specifically selected and processed acoustic stimuli increases neural regulation of middle-ear structures to: dampen the perception of background low-frequency sounds, potentiate the extraction of human voice, functionally calm the behavioral and physiological state by increasing vagal regulation of the heart, and/or promote more spontaneous social engagement behaviors. In this way, the disclosed systems and methods may trigger neural mechanisms that regulate the entire social engagement system, including enhanced vagal regulation of bodily organs.

Figure 2:
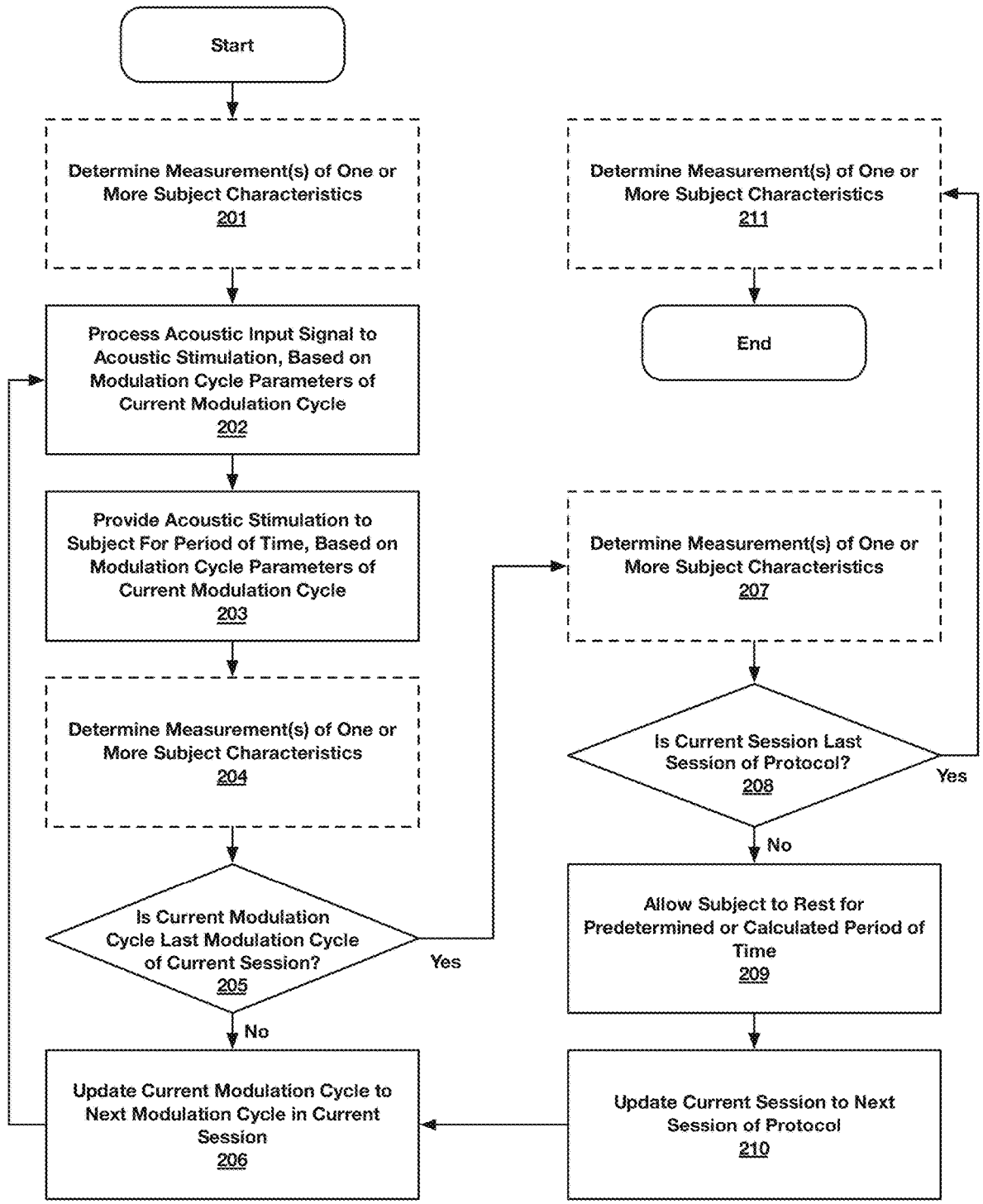
FIG. 2 shows a schematic diagram of an exemplary method according to an embodiment.

Referring to FIG. 2, an exemplary method according to an embodiment is illustrated. As shown, acoustic stimuli is presented to a subject during any number of sessions of an exemplary listening protocol adapted to recruit the function of the subject's middle-ear muscles. Generally, one or more characteristics of the subject may be measured at various times before, during and/or after the protocol and one or more user responses (e.g., functional enhancement of neural regulation of the middle-ear muscles, improved auditory processing and/or any vagal regulation of the heart) may be determined by, for example, contrasting such measurements. As discussed in detail below, in certain embodiments, any of the measurements and/or determined user responses may be employed to dynamically adjust one or more protocol parameters, such as but not limited to: a total number of sessions, a duration of one or more sessions, and/or parameters of the acoustic stimuli presented to the subject during one or more sessions.

In a first optional step 201, one or more of a subject's characteristics may be measured, observed or evaluated. In one embodiment, a structured questionnaire may be completed by, for example, a parent, guardian, teacher, doctor, or peer of the subject. Exemplary questionnaires may target specific categories of the subject's developmental and/or behavioral issues, including but not limited to, sound sensitivities and/or difficulties in interpreting the emotional state of others. Such questionnaires may focus on whether the subject has had difficulties in a specific behavioral area. Exemplary questionnaires may inquire about one or more of the following: sound sensitivity (e.g., exaggerated negative responses to common noises, such as crying or placing hands over the ears); spontaneous speech (e.g., non-prompted use of words to communicate thoughts and ideas); receptive speech (e.g., ability to understand instructions and/or phrases); spontaneity (e.g., non-prompted behaviors initiated by the subject); behavioral organization (e.g., ability to occupy oneself in a productive way when left alone); emotional control (e.g., ability to calm, ability to respond to unexpected changes without getting upset, etc.); affection (e.g., behaviors reflective of warm emotional state, such as spontaneous kissing or hugging); listening (e.g., ability to focus on human speech without visual cues); eye contact (e.g., making and maintaining eye contact); and/or relatedness (e.g., understanding of joint partnership).

Additionally or alternatively, any number of deficits in the features of a subject's social engagement system may be determined via observation, inquiry and/or physical measurement. For example, the subject may be tested to determine such characteristics as: ingestive disorders; difficulties in listening (e.g., sound sensitivities, auditory processing deficits, extraction of human voice from background sounds and/or language delays); difficulties in coordinating sucking, swallowing, vocalizing, and/or breathing; atypical intonation during vocalization (e.g., lack vocal prosody); facial expression deficits (e.g., difficulties in gaze and/or flat affect); lack of head gestures; and/or reduced vagal influences to the heart via the myelinated vagus (e.g., measured by the amplitude of RSA).

In one embodiment, cognitive ability may be determined as part of the assessment. For example, a Kaufman Brief Intelligence Test ("KBIT") may be administered. See Kaufman, A. S. et al. "Kaufman Brief Intelligence Test Manual," American Guidance Service, Circle Pines, Minn. (1990) (incorporated by reference herein in its entirety). In other embodiments, a subject's level of pain may be evaluated, for example, by administering the McGill Pain Questionnaire. See Melzack, R. "The short-form McGill pain questionnaire," Pain 30.2 (1987): 191-197 (incorporated by reference here in its entirety).

In certain embodiments, the subject may be required to participate in a semi-structured, task-based, observational assessment to determine, for example, social engagement skills. The subject may be graded on a social interaction coding scale ("SICS"), an autism diagnostic observational scale ("ADOS") and/or an early social communication coding scale ("ESCS"). As a specific example, a child may be required to participate in a ten-minute, semi-structured, play-based observational assessment with a therapist, which may be videotaped.

Auditory processing may be evaluated with a number of tests, such as the Filtered Words ("FW") and/or Competing Words ("CW") subtests from the SCAN Test for Auditory Processing Disorder. The FW subtest assesses a subject's ability to decipher human speech from background sounds, which is a component of receptive language skills. The CW subtest is a dichotic listening task, which identifies developmentally delayed or damaged central auditory pathways. See Keith, R. W. "SCAN: A Screening Test for Auditory Processing Disorders," The Psychological Corporation, San Antonio, Tex. (1986); and Keith, R. W. "SCAN-C: Test for Auditory Processing Disorders in Children—Revised," The Psychological Corporation, San Antonio, Tex. (2000) (each of which are incorporated by reference herein in its entirety).

Acoustic properties of the subject's vocalizations may be evaluated using frequency analyses (e.g., spectral analyses) and/or time-frequency analyses (e.g., modulation power spectrum analysis). These analyses can quantify the modulation of intonation (i.e., prosody) in the subject's vocalizations—an important quality in social communication.

Additionally or alternatively, a number of tests may be conducted to assess characteristics of the subject's physiological state. These tests may quantify neural regulation of autonomic state and may measure one or more of: blood pressure, heart rate, HRV, RSA and vasomotor activity. Moreover, in certain embodiments, one or more tests may be conducted to determine a level of anxiety or discomfort experienced by the patients.

A subject's heart rate, HRV and/or RSA can be measured using contact sensors, such as an electrocardiogram ("ECG") or a photoplethysmogram ("PPG"), and/or through noncontact methods. ECG may be assessed with, for example, a BIOPAC MP150 physiological acquisition system (Biopac Systems, Inc., Santa Barbara, Calif.), an EZ-IBI interbeat interval monitor (UFI, Morro Bay, Calif.), and/or a BIOLOG ambulatory heart rate monitor (UFI, Morro Bay, Calif.). A contact PPG may be assessed with, for example, a BIOPAC MP150 physiological acquisition system (Biopac Systems, Inc., Santa Barbara, Calif.) and/or a noncontact PPG may be assessed via any of the systems described in U.S. Patent App. Pub. No. 20160317041 to Porges et al. (incorporated by reference herein in its entirety). Exemplary monitoring systems may sample ECG at around 1 kHz with minimal artifact and PPG at around 100 Hz with minimal artifact.

ECG and/or heart-period data from the monitoring device(s) may be visually inspected and/or edited. Editing may comprise, for example, integer arithmetic (e.g., dividing intervals between heart beats when detections of R-wave from the ECG or pulse waves from the PPG are missed, or adding intervals when spuriously invalid detections occur).

In one embodiment, RSA may be calculated via the method, described in U.S. Pat. No. 4,510,944 to Porges (incorporated by reference herein in its entirety). This method quantifies the amplitude of RSA with age-specific parameters that are sensitive to the maturational shifts in the frequency of spontaneous breathing. In one embodiment, the method comprises the following steps: (1) R-R intervals or pulse-to-pulse intervals are timed to the nearest millisecond to produce a time series of sequential heart periods (i.e., the time between heart beats); (2) sequential heart periods are resampled into 250 ms intervals to produce time-based data; (3) the time-based series is detrended by a 51-point cubic moving polynomial that is stepped through the data to create a smoothed template and the template is subtracted from the original time-based series to generate a detrended residual series; (4) the detrended time series is bandpassed to extract the variance in the heart period pattern associated with spontaneous breathing (e.g., about 0.12 to about 1.0 Hz, depending on age); and (5) the natural logarithm of the variance of the bandpassed time series is calculated as the measure of the amplitude of RSA.

Heart period is a composite variable that is influenced by neural tone via both the parasympathetic and sympathetic branches of the autonomic nervous systems. This variable is, in part, determined by the size of the heart, which imposes limits on the temporal parameters of electrical potentials arising from a myocardium manifested in an ECG. The maturational increase in body size is paralleled by a decrease in heart rate (i.e., increase in heart period), reflecting the expanded time necessary to complete a heartbeat.

Figure 3:
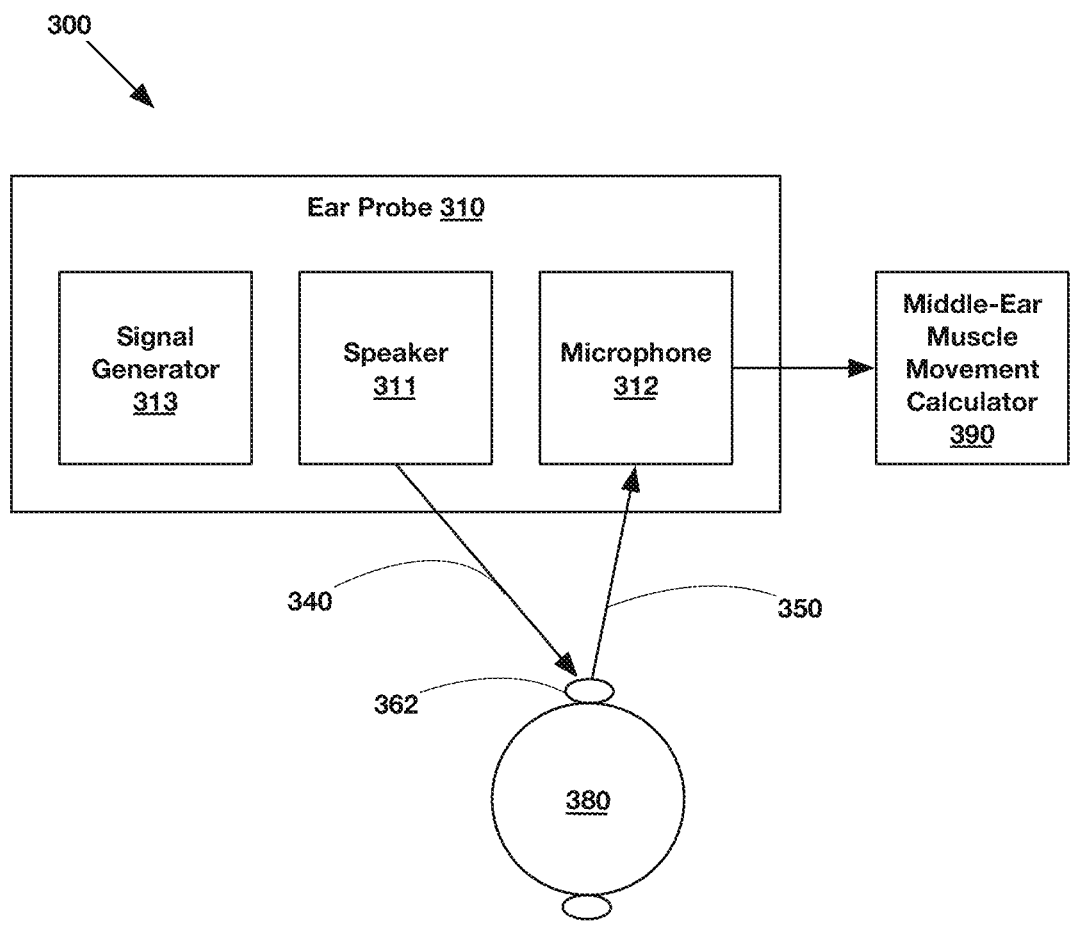
FIG. 3 shows an exemplary middle-ear sound absorption ("MESA") system 300 according to an embodiment.

In one embodiment, a subject's middle-ear transfer function may be assessed using a MESA system, as illustrated in FIG. 3. Generally, a MESA system 300 may be employed to characterize or evaluate a subject's middle-ear transfer function by measuring one or more properties (e.g., intensity, magnitude and/or phase shift) of a sound wave reflected off the subject's eardrum.

As shown, an ear probe 310 having a speaker 311 and a microphone 312 may be placed within an ear 362 of a subject 360 such that the probe 310 is in sound-wave communication with the eardrum and middle-ear muscles of the ear 362. Within the signal generator 313, a series of sinusoidal signals may be combined by a digital processor to create a probe tone 340. This digital signal, $D_{in}$, is converted to an analog voltage and driven through the speaker 311, creating a pressure wave in the ear canal that reflects off the subject's ear 362. A reflected sound wave 350 is detected by the microphone 312 and digitized to create a time synchronous representation of the reflected probe signal, $D_{out}$. An ear-muscle movement calculator 390 receives the two digital signals ($D_{in}$ and $D_{out}$) and estimates a reflectance transfer function ("RTF"), which relates incoming sound energy within the ear canal to outgoing sound energy at the same position in the ear canal. Accordingly, the MESA system 300 allows for assessment of both supra- and sub-reflexive levels of contractions, measurement of changes in middle-ear muscle status in response to various acoustic challenges and/or determination of psychological state. In one embodiment, the MESA system disclosed in U.S. Patent App. Pub. No. 2013/0303941 to Porges et al. (incorporated by reference herein in its entirety) may be employed.

Returning to FIG. 2, after initial measurements of one or more characteristics of the subject are determined in step 201, a first treatment session may begin. As shown, an acoustic input signal may be processed by an audio processing device such that acoustic stimuli is produced 202 and eventually transmitted to the subject 203. Generally, the acoustic input signal may be processed (i.e., modulated) to produce acoustic stimuli designed to exercise the neural regulation of the middle-ear structures and muscles of the subject.

In one embodiment, the acoustic input signal may comprise one or more of pre-recorded human speech, human singing, instrumental music, synthesized music and combinations thereof. For example, the input signal may have acoustic properties similar to a mother singing a lullaby to infant. Prerecorded vocal or instrumental music may be selected based on a number of variables, such as but not limited to: frequency band, modulation of intonation within the frequency band, tempo, volume and/or modulation of volume.

Certain soundtracks of animated movies (e.g., those created by The Walt Disney Company and its subsidiaries) provide an example of the optimal acoustic features for input acoustic stimulation. Such soundtracks emphasize melodic voices above middle C (i.e., 261.6 Hz), have an upbeat tempo, vary in volume within a comfortable range and minimize the inclusion of very low and very high acoustic frequencies. Other preferred acoustic input signals include, but are not limited to, lullabies, love songs, folk music and bluegrass ballads.

In another embodiment, the acoustic input signal may not be pre-recorded. Rather, the acoustic input signal may be an environmental acoustic signal, such as audio from a video being watched by the subject or speech of a person with whom the subject is interacting (e.g., a teacher, parent, therapist, medical professional or researcher). In such embodiments, the acoustic input signal may be dynamically processed into acoustic stimuli and output to a subject in real time or near real time such that the acoustic stimuli is synchronized to the video or interaction experiences. This may allow the subject to exercise neural regulation of the middle-ear muscles while, for example, listening to music, watching videos or dynamically interacting with others (e.g., in an educational, clinical or social context).

In each case, the selected input acoustic signal is processed to produce acoustic stimuli such that frequencies within a defined bandwidth are emphasized. To that end, the input acoustic signal may be processed to acoustic stimuli by attenuating frequencies outside an emphasized bandwidth (i.e., by filtering frequencies above a high-frequency limit and/or below a low-frequency limit).

Generally, the frequency characteristics of the acoustic stimuli may be selected to emphasize the frequency band in which information related to human speech is conveyed, consistent and overlapping with the documented frequency band and weights associated with the Index of Articulation ("AI") as defined in American National Standard ANSI S3.5-1997 American National Standard ANSI S3.5-1997 ("Methods for Calculation of the Speech Intelligibility Index") and/or the Speech Intelligibility Index ("SII") as described in Pavlovic, C. V. "Derivation of primary parameters and procedure's for use in speech intelligibility predictions," J. Acoust. Soc. Am. 82 (1987): 413-422 (each of which is incorporated by reference herein in its entirety). The AI is a quantified expression of the proportion of the average speech signal that is audible to a person in a given environment and is expressed on a scale of 0 to 1.0, with 1.0 representing perfect audible speech. The SII quantifies the intelligibility of speech and it is also expressed on a scale of 0 to 1.0.

Such indices emphasize the relative importance of specific frequencies in conveying information related to cues about the human nervous system that are embedded in human vocalizations and that foster the regulation of autonomic and behavioral state. During "normal" listening to human speech, the middle-ear muscles are contracted to stiffen the ossicle chain and to optimize the extraction of human voice from background sounds (e.g., via descending central mechanisms). In a "normal" ear, acoustic energy within the primary frequencies of these indices is not attenuated (or is minimally attenuated) and may pass through the middle-ear structures to the inner ear.

In one embodiment, the acoustic stimuli may be conceptualized as providing a "treadmill" exercise for the middle-ear muscles during which the demands to listen to, and process, the acoustic features of acoustic stimuli dynamically change. A traditional treadmill can dynamically adjust the walking and/or running speed and slope as the user of the treadmill is exercising. Treadmills can be programmed with a variety of exercise routines, with the speed and/or slope changing at defined times. Similarly, the acoustic stimuli may comprise dynamic challenges for the middle-ear muscles as the descending neural pathways adjust the middle-ear muscles in response to the changing processing demands required by the input acoustic stimuli during a single session or across multiple sessions.

To that end, the acoustics stimuli provided to a subject may be adjusted continuously or discretely throughout a session (and across multiple sessions). In preferred embodiments the acoustic stimuli is processed from the input acoustic signal via a number of sequential, episodic bandwidth modulations or "modulation cycles." Such modulation cycles may be seamlessly connected in time and implemented over the duration of a session.

Generally, each modulation cycle comprises at least an adjustment from a first modulation to any number of additional modulations, and an adjustment back to the first modulation. A modulation cycle may start with a minimum bandwidth and dynamically shift to broader bandwidths until a maximum bandwidth is reached. The modulation cycle may then continue to shift to narrower bandwidths until finally returning to the minimum bandwidth. For example, a modulation cycle may comprise: starting at a first, narrow modulation; adjusting from the first modulation to a wider, second modulation; adjusting from the second modulation to a widest, third modulation; adjusting from the third modulation back to the second modulation; and finally adjusting from the second modulation back to the first modulation.

Accordingly, modulation cycles may be defined by modulation cycle parameters, including: duration, a minimum frequency, a maximum frequency, a narrowest bandwidth, a widest bandwidth, individual changes in range of frequencies (i.e., modulations) and/or slope of the changes in frequencies. It will be appreciated that the minimum and maximum frequencies of a modulation within a given modulation cycle may define the modulation cycle's bandwidth at any given time, and the duration of each modulation determines the slope of the modulation cycle.

In preferred embodiments, each modulation cycle may begin and end with a narrow frequency modulation bandwidth defined by a low-frequency limit of from about 600 Hz to about 900 Hz (e.g., about 800 Hz) and a high-frequency limit of from about 1,400 Hz to about 2,000 Hz (e.g., about 1,500 Hz). Accordingly, the center frequency of each modulation cycle may be approximately equal to the resonant frequency of the middle ear in humans (i.e., about 800 Hz to about 1,200 Hz).

Exemplary modulation cycles may emphasize bandwidths within a low-frequency limit of from about 200 Hz to about 1,000 Hz (e.g., about 300 Hz, about 400 Hz, about 500 Hz, about 600 Hz, about 700 Hz, about 800 Hz, about 900 Hz or about 1,000 Hz) and a high-frequency limit of from about 1,200 Hz to about 5,000 Hz. A number of exemplary modulation cycles and corresponding emphasized bandwidths are shown in FIGS. 5-16 and Tables 1-12, below. It will be appreciated that acoustic information in an input acoustic signal that is outside the emphasized bandwidth of any given modulation cycle may be attenuated (i.e., such information will not be included in the acoustic stimuli presented to the subject).

The modulation cycles employed in exemplary methods are generally selected to enable acoustic energy to be effectively transmitted across middle-ear structures of humans, regardless of the neural tone to the middle-ear muscles. However, it will be appreciated the described methods may also be useful for non-human subjects (e.g., for calming a dog or cat before a veterinary procedure) and such modulation cycles may be adapted for these non-human subjects by modifying the center frequency according to properties of their middle-ear structures. In such cases, the modulation cycles may comprise a bandwidth approximately defined by the following equation:

$$\pm 0.7 \times \log_{10}(\text{resonant frequency})$$

The duration of each modulation cycle may be framed within the timing of neural regulation of the autonomic nervous system that is inherent in the rhythms of normal homeostasis (e.g., respiration, blood pressure, intracranial fluid, and/or vasomotor activity). For example, the duration of a given modulation cycle may range from about 60 seconds (1 minute) to about 300 seconds (5 minutes) (e.g., about 60 seconds, about 90 seconds, about 120 seconds, about 150 seconds, about 180 seconds, about 210 seconds, about 240 seconds, about 270 seconds or about 300 seconds. And the duration of each modulation within a modulation cycle may range from about 5 seconds to about 90 seconds, typically from about 10 seconds to about 30 seconds (e.g., about 10 seconds, about 15 seconds, about 20 seconds, about 25 seconds or about 30 seconds).

It will be appreciated that the number of modulation cycles and/or the parameters of each modulation cycle may vary within a session and across multiple session. Similarly, each modulation cycle may include any number of modulations comprising varying durations and/or bandwidths.

In one embodiment, the number of modulation cycles and/or the parameters of each modulation cycle within a session may be predetermined. In this case, the duration of each modulation cycle may be predetermined and informed by endogenous physiological rhythms associated with homeostatic processes (e.g., breathing, vasomotor and blood pressure oscillations). In other embodiments, the number of modulation cycles and/or the parameters of each modulation cycle within a session may be dynamically determined based on user response to the acoustic stimuli (e.g., measurement(s) of one or more characteristics of the subject and/or one or more determined subject results).

In any event, at step 202, the acoustic input signal is processed to acoustic stimuli based on modulation cycle parameters of a first modulation cycle of a first session. As explained above, the modulation cycle parameters provide the algorithm to process acoustic stimuli. Importantly, such processing is independent of the input acoustic signal.

At step 203, the acoustic stimuli processed according to the first modulation cycle parameters is provided to the subject (e.g., via a listening device). Exemplary listening device may include headphones, circumaural headphones, earphones, one or more external speakers, an integrated or external display and/or a virtual reality device. The listening device may be adapted to output acoustic stimuli to the subject with or without synchronized video.

In one embodiment, a listening device may be placed in electrical communication (e.g., wired or wireless) with an acoustic stimuli output device. The output device may receive an acoustic input signal, perform modulation, and output acoustic stimuli to the listening device. Alternatively, the output device may simply read and/or receive pre-recorded acoustic stimuli and provide the same to the listening device without further modulation of the acoustic stimulation. The listening device may receive the acoustic stimulation and output the same to a subject via one or more speakers.

In another embodiment, a listening device may be configured to receive an acoustic input signal from an audio output device and/or via a microphone. The listening device may comprise electronic circuitry adapted to receive the acoustic input signal, perform modulation on the same, and output acoustic stimuli to a subject via one or more speakers. It will be appreciated that the listening device may process the input signal in substantially real time, according to the principles discussed above.

In certain embodiments, the acoustic stimuli may be either monophonic or stereophonic. In a monophonic mode, the same acoustic features are simultaneously delivered to both ears. In a stereophonic mode, human vocalization may be delivered to one ear (e.g., the right ear) and acoustic stimuli without human vocalization may be delivered to the other ear (e.g., the left ear). In this case, the acoustic stimuli provided to each ear may be processed to pass acoustic features in the same bandwidth or different bandwidths. Moreover, the relative loudness of the left and right channels may be manipulated by the system together or independently, as desired or required. This lateralization is consistent with the neurophysiology that supports a right-ear advantage for the processing of speech.

In one embodiment, the volume may not be manipulated, as vocal music already varies in volume. By varying the bandwidth, the total acoustic energy is varied in addition to the original volume shifts. Accordingly, equipment may be set to a peak sound pressure level (e.g., about 70 dB). In other embodiments, the volume may be varied as desired or required.

It will be appreciated that the context in which the protocol is performed influences the ability to actively recruit the neural regulation of the middle-ear muscles. The context should be quiet and safe to convey cues to the nervous system to calm the subject's autonomic state. Cues and background noises can trigger shifts in autonomic state that support defense and adaptively reduce the neural tone to the middle ear muscles. In addition, social support, by a parent, friend, or therapist, may be necessary to send cues of safety to the subject's nervous system to facilitate the recruitment of the neural regulation of the middle muscles via the invention.

Generally, the duration of each session may be limited to ensure that the fast-twitch middle-ear muscles do not fatigue. In one embodiment, each session may be from about 10 minutes to about 90 minutes and, more specifically, from about 30 minutes to about 75 minutes (e.g., about 30 minutes, about 45 minutes, about 60 minutes or about 75 minutes). In certain embodiments, the length of each session may differ (e.g., the sessions may get progressively longer or shorter during the protocol). Similarly, each session may differ in one or more additional session parameters, such as: input audio signal characteristics and acoustic stimuli characteristics (e.g., number of modulation cycles and/or parameters of each modulation cycle).

In any event, upon completing the first modulation cycle (i.e., the "current modulation cycle"), a determination may be made as to whether the current modulation cycle is the last modulation cycle in the current session 205. If the current modulation cycle is not the last modulation cycle in the current session, the method may update the current modulation cycle to the next modulation cycle in the current session (step 205) and then return to step 202 to process the input acoustic signal according to the parameters of the next modulation cycle.

However, if the current modulation cycle is the last modulation cycle of the current session, the method may proceed to step 208, where a determination is made as to whether the current session is the last session of a given protocol. Generally, the duration and timing of an exemplary protocol is designed to deal with fatigue and provide sufficient exercises over an entire selected bandwidth. Accordingly, in certain embodiments, the training protocol may end after a predetermined number of sessions or, as discussed in detail below, upon achieving a desired user response.

If the current session is not the last session of the protocol, the subject may be allowed or required to rest for a predetermined and/or calculated period of time (step 209) before beginning the next session. Generally, one or more sessions may occur each day, and sessions may occur on sequential days or may be spaced apart by a certain number of days. As an example, a protocol may comprise five, one-hour sessions each separated by a rest period of at least 12 hours. As another example, a protocol may comprise ten, thirty-minute sessions, with two sessions occurring on each of five sequential days. In this example, a rest period of about 30 minutes to about 2 hours may be required between the two sessions on any given day.

The method may then proceed to step 210 by updating the current session to the next session in the protocol. The method then returns to step 206 to update the current modulation cycle to the first modulation cycle in the subsequent session (i.e., the updated current session) in order to process acoustic stimulation according to the parameters of the updated modulation cycle at step 202.

However, if the current session is determined to be the last session of a protocol in step 208, an updated measurement may be determined for one or more characteristics of the subject 211 (discussed below) and then the method may end.

As shown in FIG. 2, measurements of one or more characteristics of the subject may be observed or calculated at various times throughout the method (e.g., steps 201, 204, 207 and 211) and such measurements may be compared/contrasted to determine one or more user responses to the training protocol. Generally, such measurements and user responses may be employed to adjust various protocol parameters, such as but not limited to a number of sessions, session parameters of one or more sessions (e.g., session duration, acoustic input signal selection and/or acoustic stimuli processing parameters).

As discussed in detail above, exemplary user responses may include, but are not limited to: changes in the transfer function of the middle ear structures (e.g., as measured by a MESA system 300); changes in auditory processing (e.g., measured by the FW or CW SCAN subtests); changes in vocal prosody (e.g., measured by modulation power spectrum analyses of vocalizations); changes in autonomic state (e.g., measured by HRV or RSA); changes in facial expressivity (e.g., measured by facial electromyograms or facial coding); changes in sleep pattern; changes in sound sensitivities; changes in self-reported affective state; changes in defensive self-protecting behaviors; and/or changes in other features of the social engagement system. Additionally or alternatively, subjective assessments may be employed to determine participant fatigue (i.e., from use of middle-ear muscles) and/or any itching in the participant's ear (i.e., from middle-ear bones moving and shifting the orientation of the ear drum).

It will be appreciated that useful information may be determined by simply testing functional and/or neurophysiological-based outcomes, in the absence of a comparison to other measurements. Functional outcomes include subjective and/or objective indices of auditory hypersensitivities and auditory processing, and may be tested as described above (e.g., via FW and CW tests). Neurophysiological-based outcomes include physiological state and the measurement of the middle-ear transfer function, and such outcomes may also be determined as described above.

In one embodiment, initial measurements may be determined at step 201 and such measurements may be employed in subsequent comparisons. In certain embodiments, the initial measurements may be employed to set up initial protocol parameters and/or initial session parameters.

Measurements and/or user responses may additionally or alternatively be determined at step 204. Such information may be employed at step 205 to determine whether additional modulation cycles are desired or required. This information may also be used at step 202 or step 206 to dynamically modify parameters of the current session (e.g., parameters of one or more subsequent modulations cycles). Exemplary adjustments may comprise instantaneously or incrementally modifying: the parameters of one or more modulation cycles (e.g., range of frequencies, slope of the changes in frequencies, and/or duration of one or more cycles); the level of attenuation or amplification of the frequency range inside or outside the bandwidth; and/or the level of attenuation or amplification for the left or right ears Additionally or alternatively, measurements and/or user responses may be determined upon completion of one or more sessions (step 207). This information may be used, for example, at step 208 to determine whether the subject requires additional sessions (e.g., in embodiments where the number of sessions is dynamically determined based on achieving a desired user response). Such information may also be employed to adjust parameters for a subsequent session.

Finally, measurements and/or user responses may be determined upon completion of the protocol. Such information may be employed to determine the overall effectiveness of the protocol in reducing sound sensitivities, improving behavioral and/or autonomic state regulation, and/or reducing auditory processing deficiencies and/or reducing social engagement deficiencies in the subject. Moreover, this information may be used to evaluate other plausible mechanisms leading to behavioral and autonomic state regulation difficulties, auditory hypersensitivities, and/or auditory processing difficulties).

Figure 4:
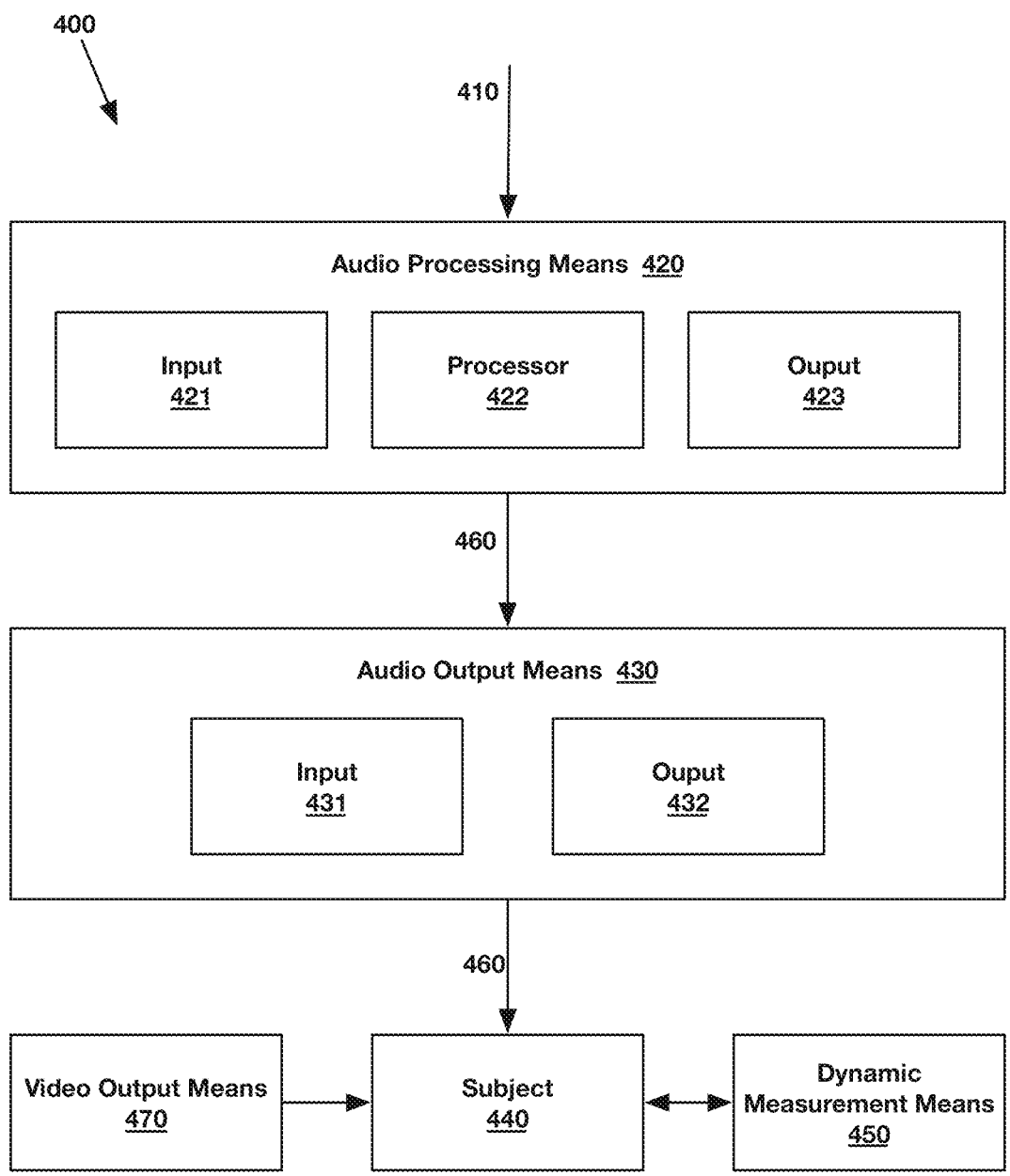
FIG. 4 shows a system architecture according to an exemplary embodiment.
Figure 5:
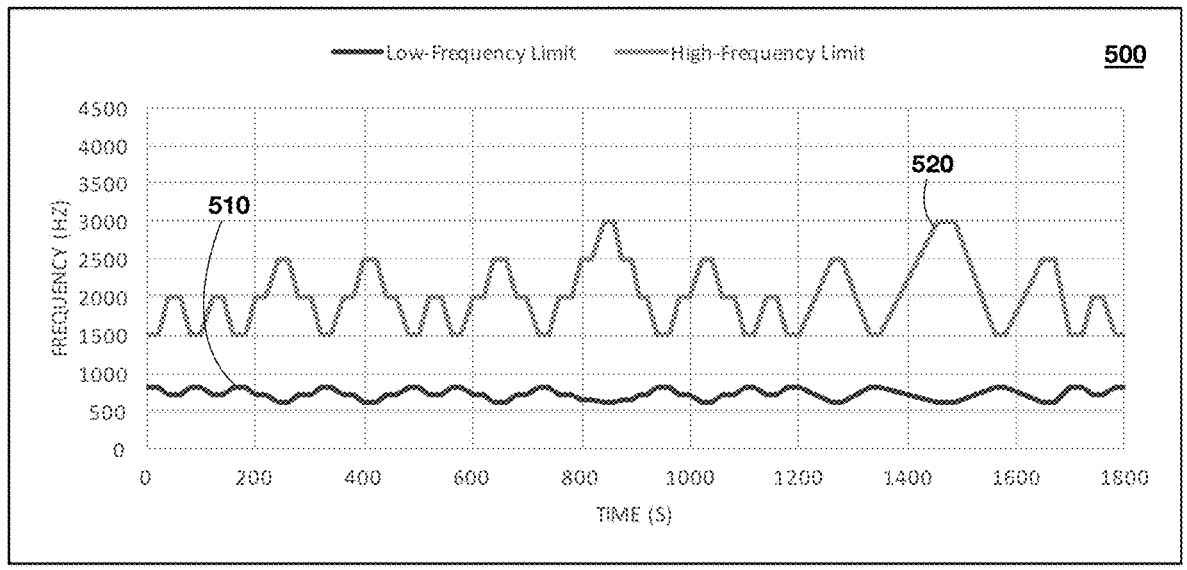
FIGS. 5-13 show graphical representations of exemplary frequency modulation cycles employed to process an acoustic input signal to acoustic stimuli that is transmitted to a subject during a first session (FIG. 5), second session (FIG. 6), third session (FIG. 7), fourth session (FIG. 8), fifth session (FIG. 9), sixth session (FIG. 10), seventh session (FIG. 11), eighth and ninth sessions (FIG. 12) and a tenth session (FIG. 13) of a training protocol according to an embodiment.
Figure 6:
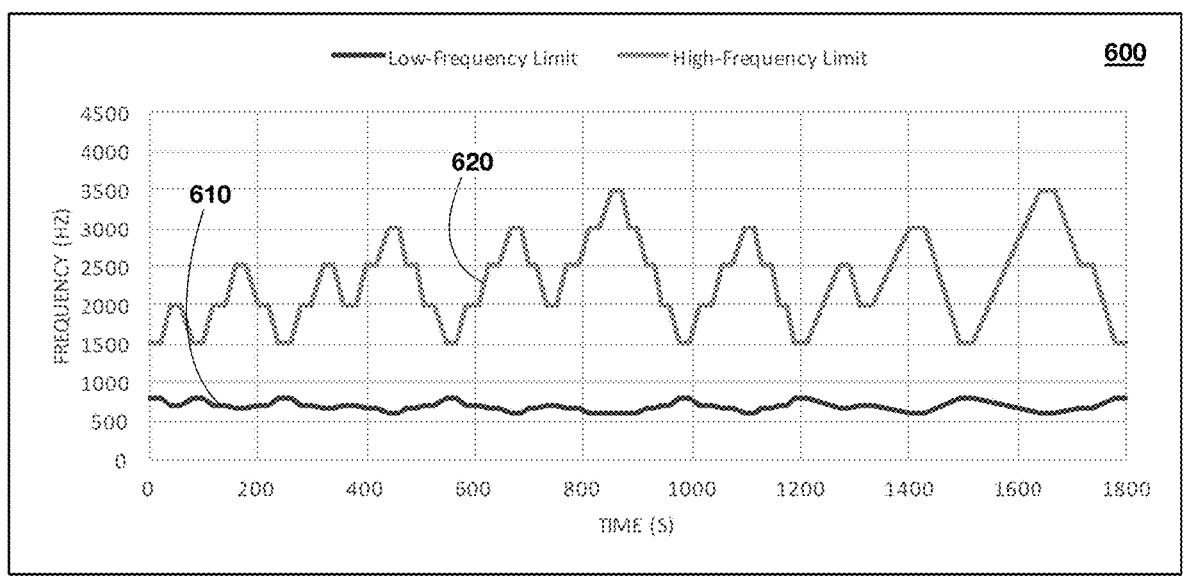
Figure 7:
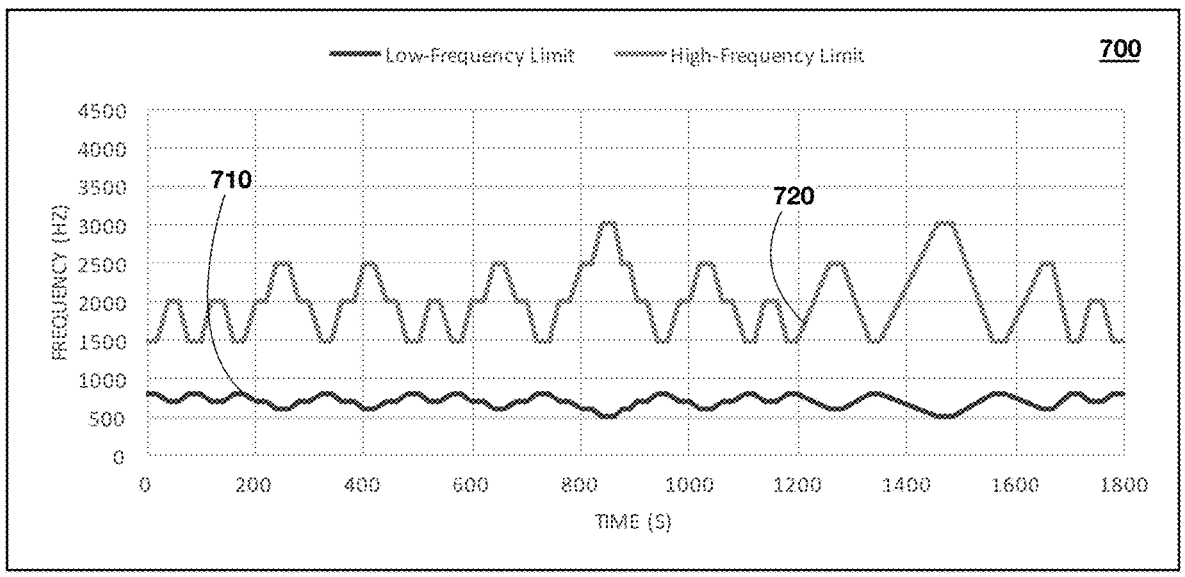
Figure 8:
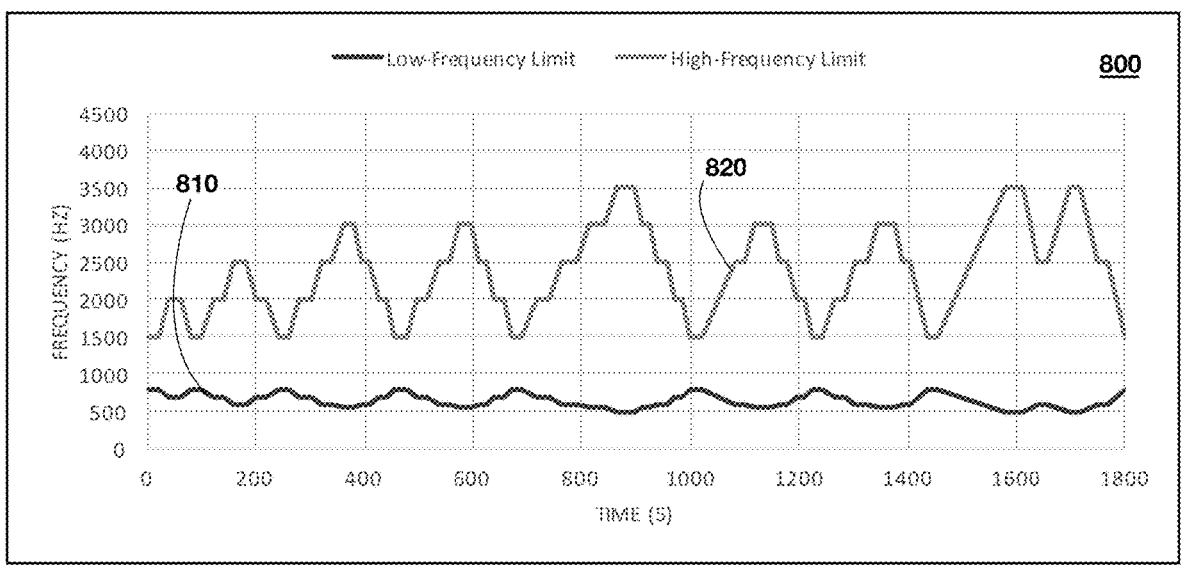
Figure 9:
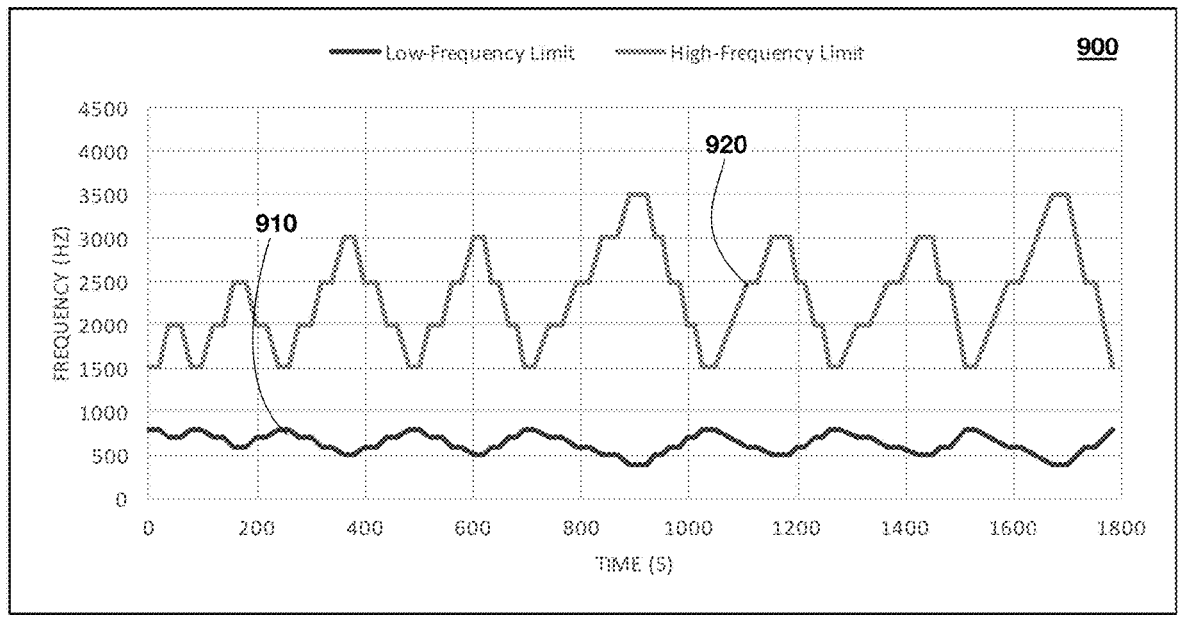
Figure 10:
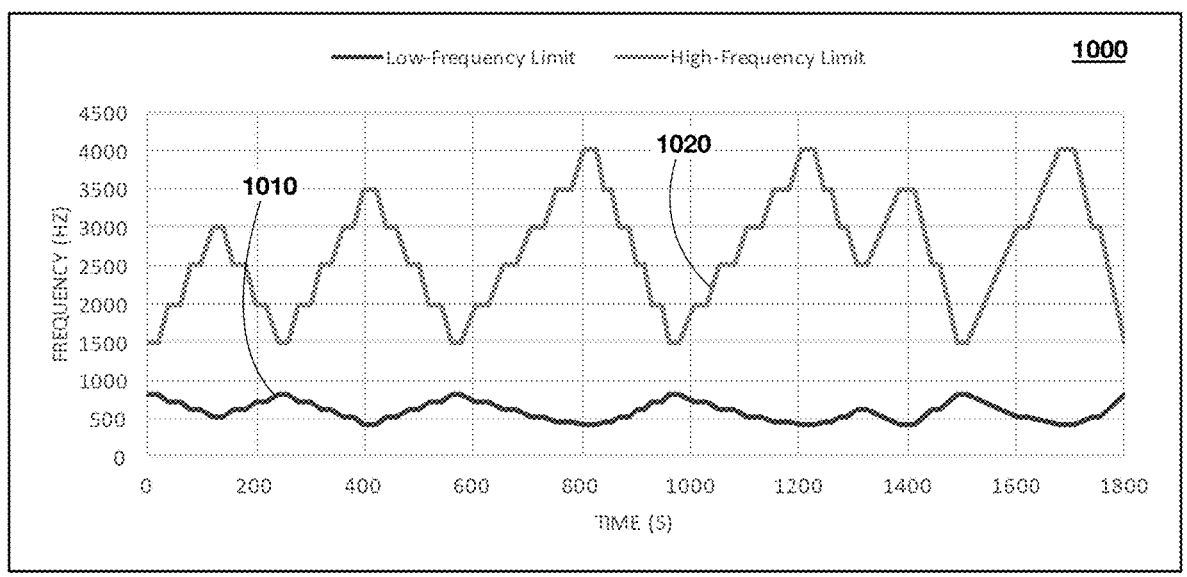
Figure 11:
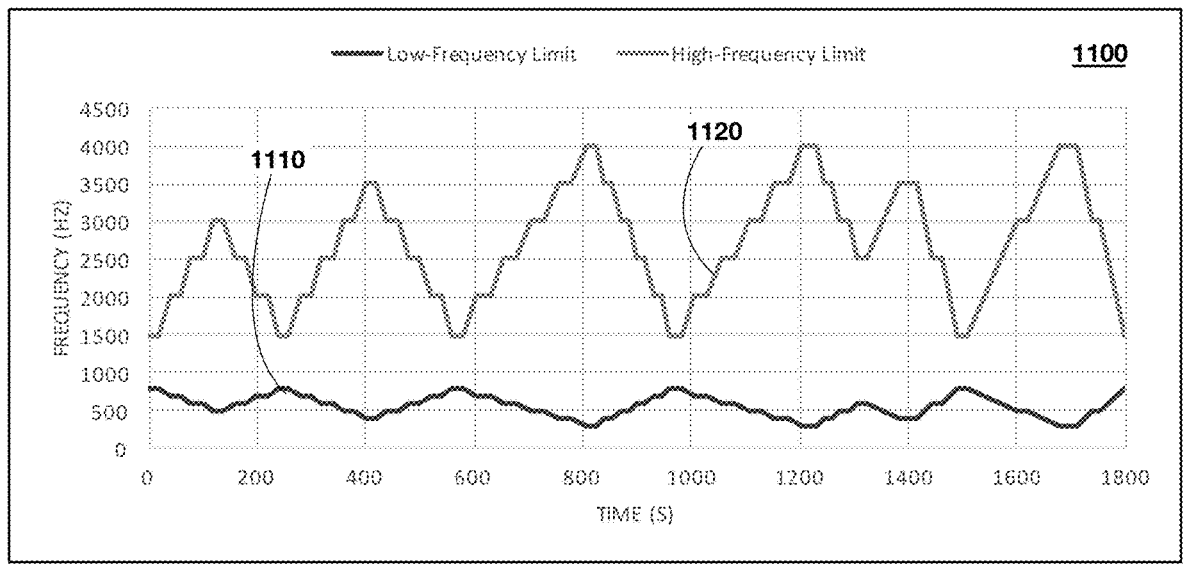
Figure 12:
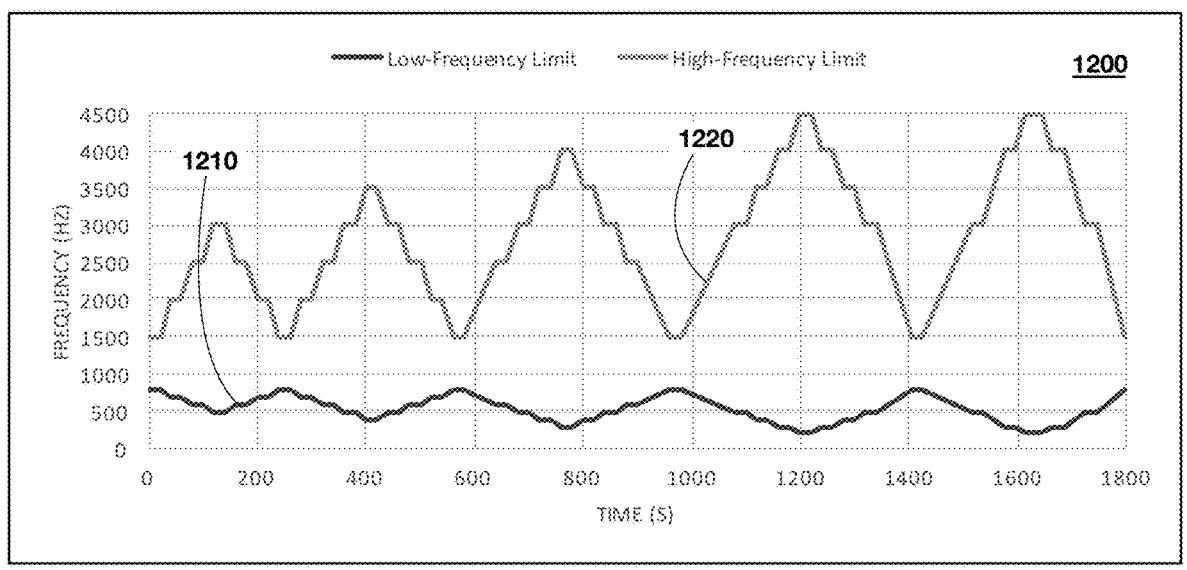
Figure 13:
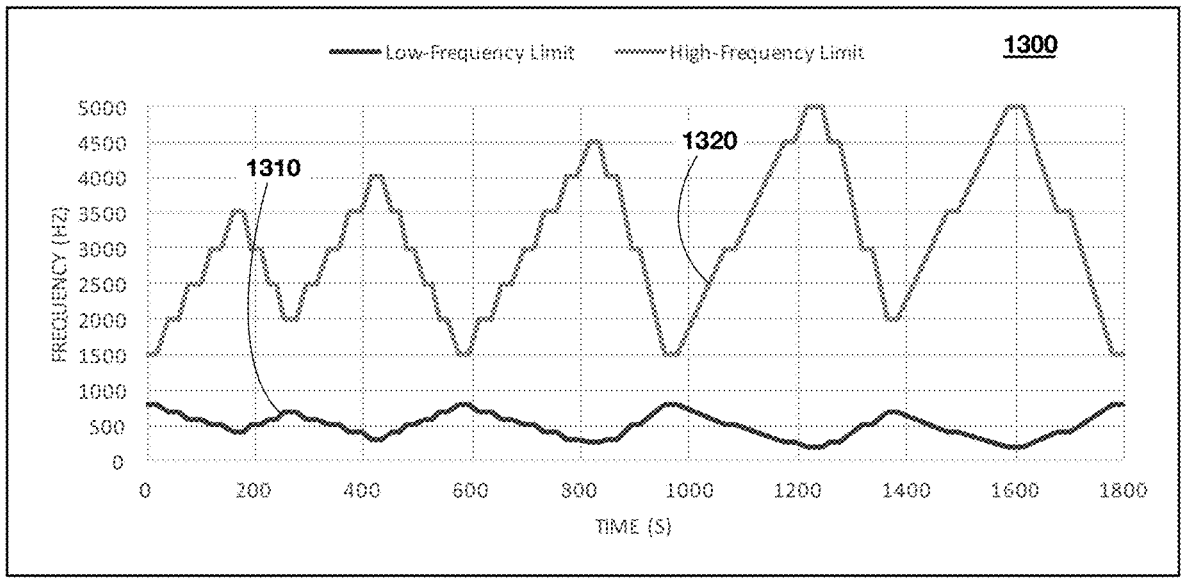

Referring to FIG. 4, an exemplary system 400 according to an embodiment is illustrated. Generally, the system 400 is configured to present acoustic stimuli 460 to a subject 440, optionally based on dynamic measures of physiological state that are used as part of a feedback system to inform the features of the stimuli being presented. This system comprises an audio processing means 420, an audio output means 430 and a dynamic measurement means 450. In one embodiment, the system may, optionally, comprise a video output means 470.

The audio processing means 420 is configured to receive an acoustic input signal 410 (e.g., via an input 421), such as but not limited to, pre-recorded or live human speech, human singing, and/or human vocal music. The acoustic input signal 410 may also be an environmental acoustic signal, such as audio synchronized to a video being currently watched by the subject, or speech of a person the subject with whom the subject is interacting (e.g., in real time or near real time).

The audio processing means 420 processes the input acoustic signal 410 (e.g., via a processor 422) according to the principles outlined herein to produce a processed acoustic signal 460. As discussed in detail above, such processing may be dependent on dynamically changing parameters, including but not limited to: frequency bandwidth, range of bandwidth changes, slope of bandwidth changes, and/or duration of modulation. These parameters are based on the characteristics of the middle-ear structures and muscles, and may be tailored to the individual subject 440 or patient. The audio processing means may be further configured to process the acoustic input signal 410 based on the output of a dynamic measurement means 450. Upon processing the input acoustic signal 410 to a processed acoustic signal 460, the audio processing means may output the same to an audio output means 430 (e.g., via an output 423).

The audio output means 430 may be configured to present the processed acoustic signal 460 to a subject 440 during a protocol session. The audio output means 430 may comprise an input 431 to receive the processed acoustic signal 460 from the audio processing means 420. The audio output means 430 may further comprise an output device 432, such as but not limited to one or more output transducers or speakers. In certain embodiments, the audio output means 430 may be headphones, circumaural headphones and/or earphones.

Although shown as separate components, it will be appreciated that any of the audio processing means 420, audio output means 430 video output means 470 and/or dynamic measurement means 450 may be combined into a single device. For example, a combined audio processing/audio output device may be a pair of headphones with a processor configured to perform the required audio processing.

As another example, in embodiments where the system comprises a video output means 470, such as a television, computer monitor and or VR device (e.g., a 360° video platform), the video output means may provide the acoustic input signal 410 processed by the audio processing means 420. Additionally or alternatively, the video output means 470 may comprise a processor configured to perform the required audio processing of the audio processing means 420 and/or speakers to output the processed audio signal 460 to the subject 440. Functionally, the simultaneous observation of facial and head movements, while listening to human vocalizations, may improve speech intelligibility. Accordingly, a VR environment may be provided wherein one or more humans are shown to be speaking or singing the acoustic stimuli 460 presented to the subject 440 with appropriate facial, head and/or hand movements. Such VR environment may require movements by the subject 440 to stimulate physiological states.

The dynamic measurement means 450 may be configured to sense one or more physiological parameters of the subject 440. As discussed above, these physiological parameters may include the subject's heart rate, RSA, vasomotor activity, and/or measures of the transfer function of the middle ear. For example, the transfer function of the middle ear may be tested using a MESA system (see FIG. 3 at 300), the subject's heart rate and RSA may be tested with an ECG or PPG, and vasomotor activity may be tested with a PPG.

After an assessment of the subject is performed via the dynamic measurement means 450, results of the assessment may be used to adjust the processing that occurs in audio processing means 420. This adjustment may alter the bandwidth and other features of one or more modulation cycles and/or a sequence of modulation cycles within one or more sessions according to the principles discussed above.

Referring to FIGS. 5-13, graphical representations of exemplary frequency modulation cycles employed to process an acoustic input signal to acoustic stimuli that is transmitted to a subject during a first session (FIG. 5), second session (FIG. 6), third session (FIG. 7), fourth session (FIG. 8), fifth session (FIG. 9), sixth session (FIG. 10), seventh session (FIG. 11), eighth and ninth sessions (FIG. 12) and a tenth session (FIG. 13) of a training protocol is illustrated. As shown, the x-axis of each graph (i.e., 500, 600, 700, 800, 900, 1000, 1200 and 1300) represents time in seconds and the y-axis indicates frequency. The bandwidth of each modulation cycle may be defined by the low-frequency limit (510, 610, 710, 810, 910, 1010, 1110, 1210 and 1310) and the high-frequency limit (520, 620, 720, 820, 920, 1020, 1120, 1220, 1320 and 1420) in each graph, respectively. Details of each of the modulation cycles shown in FIGS. 5-13 are respectively provided in Tables 1-9 of Appendix A.

Figure 14:
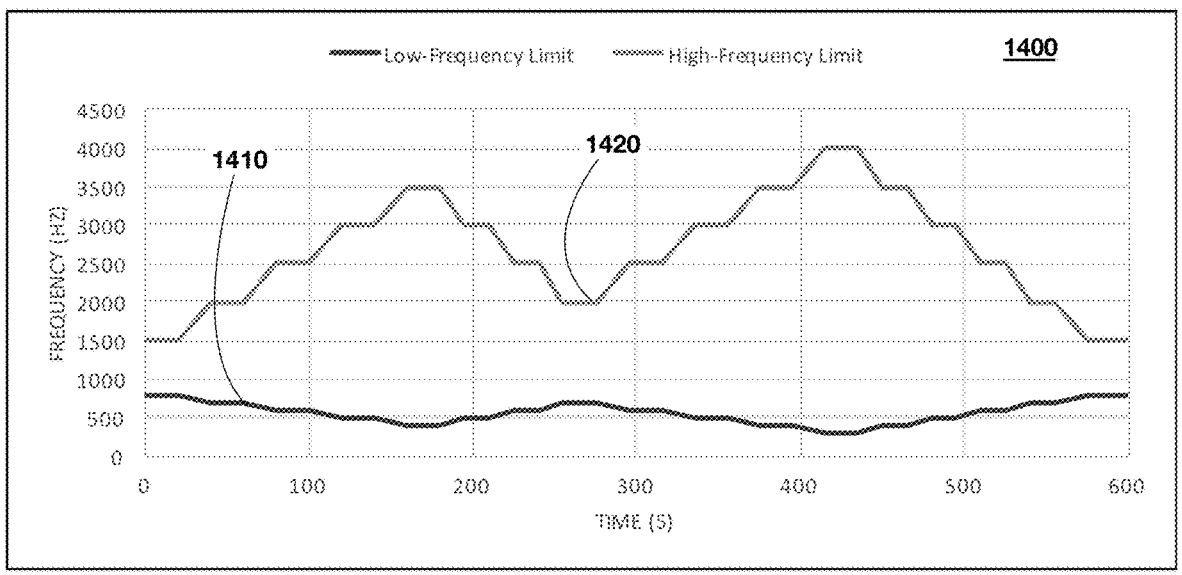
FIGS. 14-16 show graphical representations of exemplary frequency modulation cycles employed to process an acoustic input signal to acoustic stimuli that is transmitted to a subject during three exemplary booster sessions according to an embodiment.
Figure 15:
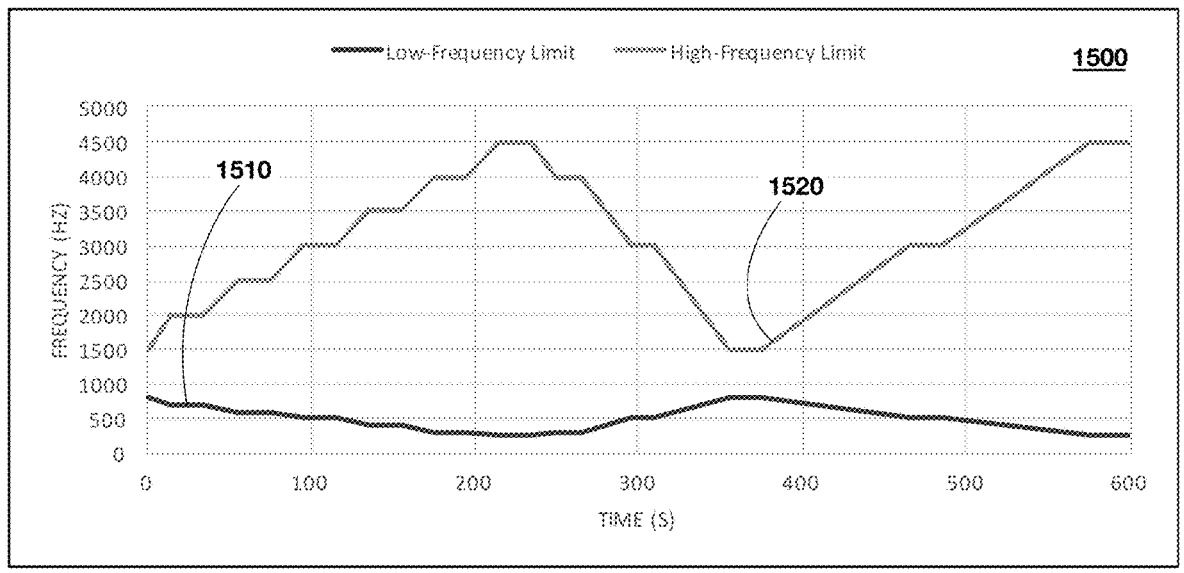
Figure 16:
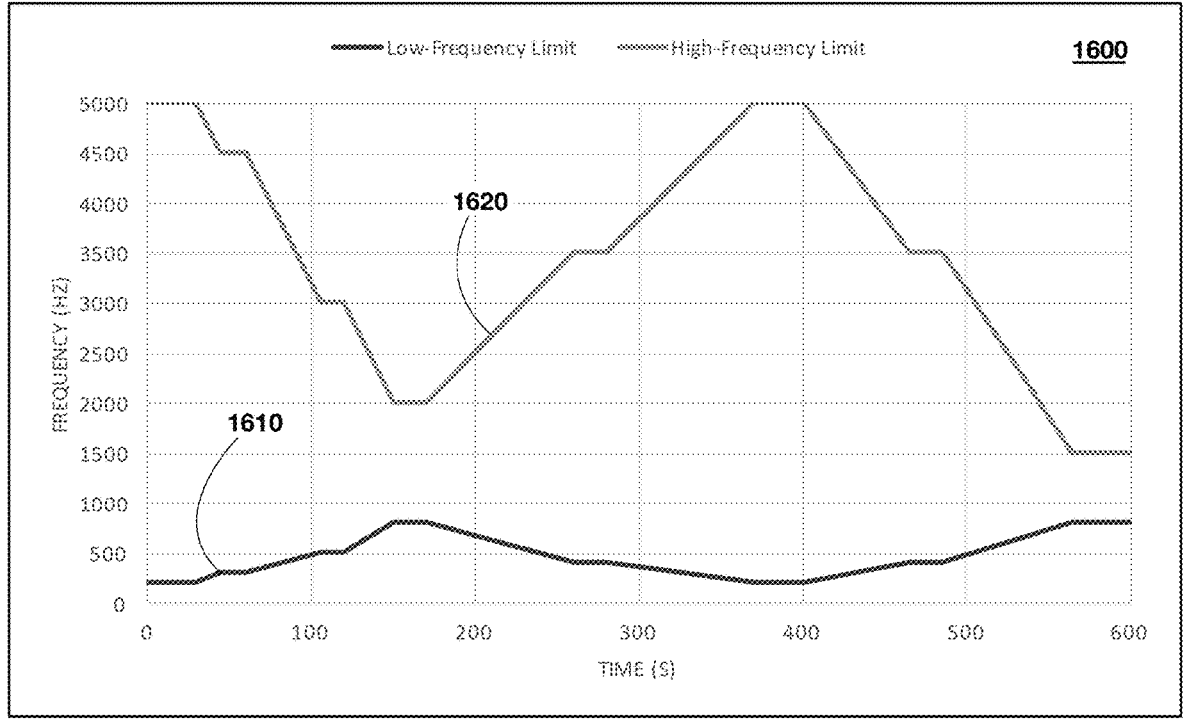

Referring to FIGS. 14-16, graphical representations of modulation cycles within a first booster session (FIG. 14), a second booster session (FIG. 15) and a third booster session (FIG. 16) are illustrated, where the x-axis of each graph (i.e., 1400, 1500 and 1600) represents time in seconds and the y-axis indicates frequency. In certain embodiments, a subject who has completed a protocol may be treated with one or more so-called "booster sessions" to re-engage the subject's social engagement system. Such booster sessions may be appropriate if, for example, a subject experiences a loss of any of any benefits received from a previously completed protocol (e.g., after a long period of time and/or upon the occurrence of an event, such as a traumatic experience, fever or illness).

The bandwidth of each modulation cycle may be defined by the low-frequency limit (1410, 1510 and 1610) and the high-frequency limit (1420, 1520 and 1620) in each graph, respectively. And details of each of the modulation cycles shown in FIGS. 14-16 are respectively provided in Tables 10-12 of Appendix A.

Because the described methods and systems deliver acoustic stimuli to subjects, they share some of the features of auditory intervention therapies ("AIT"). However, the disclosed methods and systems differ from traditional AIT in practice and theory. First, the methods and systems are based on the Polyvagal Theory and reflect a strategic attempt to engage neural regulation of specific structures involved in the social engagement system described by the Polyvagal Theory. Second, the methods and systems focus on features (e.g., sound sensitivities and difficulties in behavioral and autonomic state regulation, auditory processing, spontaneous social engagement, pain, anxiety etc.) that may be expressed by individuals with or without clinical diagnoses. Third, the effectiveness of the methods and systems may be measured through well-defined behavioral and physiological features of the social engagement system. Fourth, the methods and systems are designed with a number of unique features to engage and exercise the neural regulation of the middle-ear muscles, including an understanding of the transfer function of the middle-ear structures and the vulnerability of the fast-twitch middle-ear muscles to fatigue. Fifth, the duration of the described procedures may be shorter (e.g., less than 5 hours) than most forms of AIT.

Moreover, there are several problems related to the evaluation of traditional AIT. First, the neurophysiological theory underlying conventional AIT is often not well developed or tested. Second, research has been frequently structured to ask questions of efficacy instead of developing protocols to test theoretically relevant components of AIT in order to understand the mechanisms and to refine the methodology. Third, since AIT are applied within a clinical setting, several experimental design parameters are difficult to control including: a constant protocol, limiting concurrent treatments (e.g., medication), and/or randomization.

Embodiments of the subject matter and the functional operations described in this specification can be implemented in one or more of the following: digital electronic circuitry; tangibly-embodied computer software or firmware; computer hardware, including the structures disclosed in this specification and their structural equivalents; and combinations thereof. Such embodiments can be implemented as one or more modules of computer program instructions encoded on a tangible non-transitory program carrier for execution by, or to control the operation of, data processing apparatus (i.e., one or more computer programs). Program instructions may be, alternatively or additionally, encoded on an artificially generated propagated signal (e.g., a machine-generated electrical, optical, or electromagnetic signal) that is generated to encode information for transmission to suitable receiver apparatus for execution by a data processing apparatus. And the computer storage medium can be one or more of: a machine-readable storage device, a machine-readable storage substrate, a random or serial access memory device, and combinations thereof.

As used herein, the term "data processing apparatus" comprises all kinds of apparatuses, devices, and machines for processing data, including but not limited to, a programmable processor, a computer, and/or multiple processors or computers. Exemplary apparatuses may include special purpose logic circuitry, such as a field programmable gate array ("FPGA") and/or an application specific integrated circuit ("ASIC"). In addition to hardware, exemplary apparatuses may comprise code that creates an execution environment for the computer program (e.g., code that constitutes one or more of: processor firmware, a protocol stack, a database management system, an operating system, and a combination thereof).

The term "computer program" may also be referred to or described herein as a "program," "software," a "software application," a "module," a "software module," a "script," or simply as "code." A computer program may be written in any form of programming language, including compiled or interpreted languages, or declarative or procedural languages, and it can be deployed in any form, including as a standalone program or as a module, component, subroutine, or other unit suitable for use in a computing environment. Such software may correspond to a file in a file system. A program can be stored in a portion of a file that holds other programs or data. For example, a program may include one or more scripts stored in a markup language document; in a single file dedicated to the program in question; or in multiple coordinated files (e.g., files that store one or more modules, sub programs, or portions of code). A computer program can be deployed and/or executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, such as but not limited to an FPGA and/or an ASIC.

Computers suitable for the execution of the one or more computer programs include, but are not limited to, general purpose microprocessors, special purpose microprocessors, and/or any other kind of central processing unit ("CPU"). Generally, CPU will receive instructions and data from a read only memory ("ROM") and/or a random access memory ("RAM"). The essential elements of a computer are a CPU for performing or executing instructions and one or more memory devices for storing instructions and data. Generally, a computer will also include, or be operatively coupled to receive data from or transfer data to, or both, one or more mass storage devices for storing data (e.g., magnetic, magneto optical disks, and/or optical disks). However, a computer need not have such devices. Moreover, a computer may be embedded in another device, such as but not limited to, a mobile telephone, a personal digital assistant ("PDA"), a mobile audio or video player, a game console, a Global Positioning System ("GPS") receiver, or a portable storage device (e.g., a universal serial bus ("USB") flash drive).

Computer readable media suitable for storing computer program instructions and data include all forms of nonvolatile memory, media and memory devices. For example, computer readable media may include one or more of the following: semiconductor memory devices, such as erasable programmable read-only memory ("EPROM"), electrically erasable programmable read-only memory ("EEPROM") and/or and flash memory devices; magnetic disks, such as internal hard disks or removable disks; magneto optical disks; and/or CD ROM and DVD-ROM disks. The processor and the memory can be supplemented by, or incorporated in, special purpose logic circuitry.

To provide for interaction with a user, embodiments may be implemented on a computer having any type of display device for displaying information to a user. Exemplary display devices include, but are not limited to one or more of: projectors, cathode ray tube ("CRT") monitors, liquid crystal displays ("LCD"), light-emitting diode ("LED") monitors and/or organic light-emitting diode ("OLED") monitors. The computer may further comprise one or more input devices by which the user can provide input to the computer. Input devices may comprise one or more of: keyboards, a pointing device (e.g., a mouse or a trackball). Input from the user can be received in any form, including acoustic, speech, or tactile input. Moreover, feedback may be provided to the user via any form of sensory feedback (e.g., visual feedback, auditory feedback, or tactile feedback). A computer can interact with a user by sending documents to and receiving documents from a device that is used by the user (e.g., by sending web pages to a web browser on a user's client device in response to requests received from the web browser).

Embodiments of the subject matter described in this specification can be implemented in a computing system that includes one or more of the following components: a back-end component (e.g., a data server); a middleware component (e.g., an application server); a frontend component (e.g., a client computer having a graphical user interface ("GUI") and/or a web browser through which a user can interact with an implementation of the subject matter described in this specification); and/or combinations thereof. The components of the system can be interconnected by any form or medium of digital data communication, such as but not limited to, a communication network. Non-limiting examples of communication networks include a local area network ("LAN") and a wide area network ("WAN"), e.g., the Internet.

The computing system may include clients and/or servers. The client and server may be remote from each other and interact through a communication network. The relationship of client and server arises by virtue of computer programs running on the respective computers and having a client-server relationship to each other.

Various embodiments are described in this specification, with reference to the detailed discussed above, the accompanying drawings, and the claims. Numerous specific details are described to provide a thorough understanding of various embodiments. However, in certain instances, well-known or conventional details are not described in order to provide a concise discussion. The figures are not necessarily to scale, and some features may be exaggerated or minimized to show details of particular components. Therefore, specific structural and functional details disclosed herein are not to be interpreted as limiting, but merely as a basis for the claims and as a representative basis for teaching one skilled in the art to variously employ the embodiments.

The embodiments described and claimed herein and drawings are illustrative and are not to be construed as limiting the embodiments. The subject matter of this specification is not to be limited in scope by the specific examples, as these examples are intended as illustrations of several aspects of the embodiments. Any equivalent examples are intended to be within the scope of the specification. Indeed, various modifications of the disclosed embodiments in addition to those shown and described herein will become apparent to those skilled in the art, and such modifications are also intended to fall within the scope of the appended claims.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

All cited references including patents, patent applications and publications are incorporated herein by reference in their entirety and for all purposes to the same extent as if each individual publication or patent or patent application was specifically and individually indicated to be incorporated by reference in its entirety for all purposes.

APPENDIX A

TABLE 1

| Session 1 (500) | | | |
|---|---|---|---|
| Time (s) | Duration (s) | Low-Frequency Limit (Hz) | High-Frequency Limit (Hz) |
| Modulation Cycle 1 | | | |
| 0 | 20 | 800 | 1500 |
| 20 | 20 | 800 | 1500 |
| 40 | 20 | 700 | 2000 |
| 60 | 20 | 700 | 2000 |
| 80 | 20 | 800 | 1500 |
| Modulation Cycle 2 | | | |
| 100 | 20 | 800 | 1500 |
| 120 | 20 | 700 | 2000 |
| 140 | 20 | 700 | 2000 |
| 160 | 20 | 800 | 1500 |
| Modulation Cycle 3 | | | |
| 180 | 20 | 800 | 1500 |
| 200 | 20 | 700 | 2000 |
| 220 | 20 | 700 | 2000 |
| 240 | 20 | 600 | 2500 |
| 260 | 20 | 600 | 2500 |
| 280 | 20 | 700 | 2000 |
| 300 | 20 | 700 | 2000 |
| 320 | 20 | 800 | 1500 |
| Modulation Cycle 4 | | | |
| 340 | 20 | 800 | 1500 |
| 360 | 20 | 700 | 2000 |
| 380 | 20 | 700 | 2000 |
| 400 | 20 | 600 | 2500 |
| 420 | 20 | 600 | 2500 |
| 440 | 20 | 700 | 2000 |
| 460 | 20 | 700 | 2000 |
| 480 | 20 | 800 | 1500 |
| Modulation Cycle 5 | | | |
| 500 | 20 | 800 | 1500 |
| 520 | 20 | 700 | 2000 |
| 540 | 20 | 700 | 2000 |
| 560 | 20 | 800 | 1500 |

TABLE 1-continued

| Session 1 (500) | | | |
|---|---|---|---|
| Time (s) | Duration (s) | Low-Frequency Limit (Hz) | High-Frequency Limit (Hz) |
| Modulation Cycle 6 | | | |
| 580 | 20 | 800 | 1500 |
| 600 | 20 | 700 | 2000 |
| 620 | 20 | 700 | 2000 |
| 640 | 20 | 600 | 2500 |
| 660 | 20 | 600 | 2500 |
| 680 | 20 | 700 | 2000 |
| 700 | 20 | 700 | 2000 |
| 720 | 20 | 800 | 1500 |
| Modulation Cycle 7 | | | |
| 740 | 20 | 800 | 1500 |
| 760 | 20 | 700 | 2000 |
| 780 | 20 | 700 | 2000 |
| 800 | 20 | 650 | 2500 |
| 820 | 20 | 650 | 2500 |
| 840 | 20 | 600 | 3000 |
| 860 | 20 | 600 | 3000 |
| 875 | 15 | 650 | 2500 |
| 890 | 15 | 650 | 2500 |
| 905 | 15 | 700 | 2000 |
| 920 | 15 | 700 | 2000 |
| 940 | 20 | 800 | 1500 |
| Modulation Cycle 8 | | | |
| 960 | 20 | 800 | 1500 |
| 980 | 20 | 700 | 2000 |
| 1000 | 20 | 700 | 2000 |
| 1020 | 20 | 600 | 2500 |
| 1040 | 20 | 600 | 2500 |
| 1060 | 20 | 700 | 2000 |
| 1080 | 20 | 700 | 2000 |
| 1100 | 20 | 800 | 1500 |
| Modulation Cycle 9 | | | |
| 1120 | 20 | 800 | 1500 |
| 1140 | 20 | 700 | 2000 |
| 1160 | 20 | 700 | 2000 |
| 1180 | 20 | 800 | 1500 |
| Modulation Cycle 10 | | | |
| 1200 | 20 | 800 | 1500 |
| 1260 | 60 | 600 | 2500 |
| 1280 | 20 | 600 | 2500 |
| 1330 | 50 | 800 | 1500 |
| Modulation Cycle 11 | | | |
| 1350 | 20 | 800 | 1500 |
| 1455 | 105 | 600 | 3000 |
| 1485 | 30 | 600 | 3000 |
| 1560 | 75 | 800 | 1500 |
| Modulation Cycle 12 | | | |
| 1580 | 20 | 800 | 1500 |
| 1650 | 70 | 600 | 2500 |
| 1670 | 20 | 600 | 2500 |
| 1700 | 30 | 800 | 1500 |
| Modulation Cycle 13 | | | |
| 1720 | 20 | 800 | 1500 |
| 1740 | 20 | 700 | 2000 |
| 1760 | 20 | 700 | 2000 |
| 1780 | 20 | 800 | 1500 |
| 1800 | 20 | 800 | 1500 |

TABLE 2

Session 2 (600)

| Time (s) | Duration (s) | Low-Frequency Limit (Hz) | High-Frequency Limit (Hz) |
|---|---|---|---|
| Modulation Cycle 1 | | | |
| 0 | 20 | 800 | 1500 |
| 20 | 20 | 800 | 1500 |
| 40 | 20 | 700 | 2000 |
| 60 | 20 | 700 | 2000 |
| 80 | 20 | 800 | 1500 |
| Modulation Cycle 2 | | | |
| 100 | 20 | 800 | 1500 |
| 120 | 20 | 700 | 2000 |
| 140 | 20 | 700 | 2000 |
| 160 | 20 | 650 | 2500 |
| 180 | 20 | 650 | 2500 |
| 200 | 20 | 700 | 2000 |
| 220 | 20 | 700 | 2000 |
| 240 | 20 | 800 | 1500 |
| Modulation Cycle 3 | | | |
| 260 | 20 | 800 | 1500 |
| 280 | 20 | 700 | 2000 |
| 300 | 20 | 700 | 2000 |
| 320 | 20 | 650 | 2500 |
| 340 | 20 | 650 | 2500 |
| 360 | 20 | 700 | 2000 |
| 380 | 20 | 700 | 2000 |
| 400 | 20 | 650 | 2500 |
| 420 | 20 | 650 | 2500 |
| 440 | 20 | 600 | 3000 |
| 460 | 20 | 600 | 3000 |
| 475 | 15 | 650 | 2500 |
| 490 | 15 | 650 | 2500 |
| 505 | 15 | 700 | 2000 |
| 525 | 20 | 700 | 2000 |
| 545 | 20 | 800 | 1500 |
| Modulation Cycle 4 | | | |
| 565 | 20 | 800 | 1500 |
| 585 | 20 | 700 | 2000 |
| 605 | 20 | 700 | 2000 |
| 625 | 20 | 650 | 2500 |
| 645 | 20 | 650 | 2500 |
| 665 | 20 | 600 | 3000 |
| 685 | 20 | 600 | 3000 |
| 700 | 15 | 650 | 2500 |
| 715 | 15 | 650 | 2500 |
| 730 | 15 | 700 | 2000 |
| 750 | 20 | 700 | 2000 |
| 770 | 20 | 650 | 2500 |
| 790 | 20 | 650 | 2500 |
| 810 | 20 | 600 | 3000 |
| 830 | 20 | 600 | 3000 |
| 850 | 20 | 600 | 3500 |
| 870 | 20 | 600 | 3500 |
| 885 | 15 | 600 | 3000 |
| 900 | 15 | 600 | 3000 |
| 915 | 15 | 650 | 2500 |
| 930 | 15 | 650 | 2500 |
| 945 | 15 | 700 | 2000 |
| 960 | 15 | 700 | 2000 |
| 975 | 15 | 800 | 1500 |
| Modulation Cycle 5 | | | |
| 995 | 20 | 800 | 1500 |
| 1015 | 20 | 700 | 2000 |
| 1035 | 20 | 700 | 2000 |
| 1055 | 20 | 650 | 2500 |
| 1075 | 20 | 650 | 2500 |
| 1095 | 20 | 600 | 3000 |
| 1115 | 20 | 600 | 3000 |
| 1130 | 15 | 650 | 2500 |
| 1145 | 15 | 650 | 2500 |
| 1160 | 15 | 700 | 2000 |
| 1175 | 15 | 700 | 2000 |
| 1190 | 15 | 800 | 1500 |
| Modulation Cycle 6 | | | |
| 1210 | 20 | 800 | 1500 |
| 1270 | 60 | 650 | 2500 |
| 1290 | 20 | 650 | 2500 |
| 1310 | 20 | 700 | 2000 |
| 1330 | 20 | 700 | 2000 |
| 1400 | 70 | 600 | 3000 |
| 1430 | 30 | 600 | 3000 |
| 1495 | 65 | 800 | 1500 |
| Modulation Cycle 7 | | | |
| 1515 | 20 | 800 | 1500 |
| 1640 | 125 | 600 | 3500 |
| 1670 | 30 | 600 | 3500 |
| 1715 | 45 | 650 | 2500 |
| 1735 | 20 | 650 | 2500 |
| 1780 | 45 | 800 | 1500 |
| 1800 | 20 | 800 | 1500 |

TABLE 3

Session 3 (700)

| Time (s) | Duration (s) | Low-Frequency Limit (Hz) | High-Frequency Limit (Hz) |
|---|---|---|---|
| 0 | 20 | 800 | 1500 |
| 20 | 20 | 800 | 1500 |
| 40 | 20 | 700 | 2000 |
| 60 | 20 | 700 | 2000 |
| 80 | 20 | 800 | 1500 |
| Modulation Cycle 1 | | | |
| 100 | 20 | 800 | 1500 |
| 120 | 20 | 700 | 2000 |
| 140 | 20 | 700 | 2000 |
| 160 | 20 | 800 | 1500 |
| Modulation Cycle 2 | | | |
| 180 | 20 | 800 | 1500 |
| 200 | 20 | 700 | 2000 |
| 220 | 20 | 700 | 2000 |
| 240 | 20 | 600 | 2500 |
| 260 | 20 | 600 | 2500 |
| 280 | 20 | 700 | 2000 |
| 300 | 20 | 700 | 2000 |
| 320 | 20 | 800 | 1500 |
| Modulation Cycle 3 | | | |
| 340 | 20 | 800 | 1500 |
| 360 | 20 | 700 | 2000 |
| 380 | 20 | 700 | 2000 |
| 400 | 20 | 600 | 2500 |
| 420 | 20 | 600 | 2500 |
| 440 | 20 | 700 | 2000 |
| 460 | 20 | 700 | 2000 |
| 480 | 20 | 800 | 1500 |
| Modulation Cycle 4 | | | |
| 500 | 20 | 800 | 1500 |
| 520 | 20 | 700 | 2000 |
| 540 | 20 | 700 | 2000 |
| 560 | 20 | 800 | 1500 |
| Modulation Cycle 5 | | | |
| 580 | 20 | 800 | 1500 |
| 600 | 20 | 700 | 2000 |
| 620 | 20 | 700 | 2000 |
| 640 | 20 | 600 | 2500 |
| 660 | 20 | 600 | 2500 |
| 680 | 20 | 700 | 2000 |

TABLE 3-continued

Session 3 (700)

| Time (s) | Duration (s) | Low-Frequency Limit (Hz) | High-Frequency Limit (Hz) |
|---|---|---|---|
| 700 | 20 | 700 | 2000 |
| 720 | 20 | 800 | 1500 |
| Modulation Cycle 6 | | | |
| 740 | 20 | 800 | 1500 |
| 760 | 20 | 700 | 2000 |
| 780 | 20 | 700 | 2000 |
| 800 | 20 | 600 | 2500 |
| 820 | 20 | 600 | 2500 |
| 840 | 20 | 500 | 3000 |
| 860 | 20 | 500 | 3000 |
| 875 | 15 | 600 | 2500 |
| 890 | 15 | 600 | 2500 |
| 905 | 15 | 700 | 2000 |
| 920 | 15 | 700 | 2000 |
| 940 | 20 | 800 | 1500 |
| Modulation Cycle 7 | | | |
| 960 | 20 | 800 | 1500 |
| 980 | 20 | 700 | 2000 |
| 1000 | 20 | 700 | 2000 |
| 1020 | 20 | 600 | 2500 |
| 1040 | 20 | 600 | 2500 |
| 1060 | 20 | 700 | 2000 |
| 1080 | 20 | 700 | 2000 |
| 1100 | 20 | 800 | 1500 |
| Modulation Cycle 8 | | | |
| 1120 | 20 | 800 | 1500 |
| 1140 | 20 | 700 | 2000 |
| 1160 | 20 | 700 | 2000 |
| 1180 | 20 | 800 | 1500 |
| Modulation Cycle 9 | | | |
| 1200 | 20 | 800 | 1500 |
| 1260 | 60 | 600 | 2500 |
| 1280 | 20 | 600 | 2500 |
| 1330 | 50 | 800 | 1500 |
| Modulation Cycle 10 | | | |
| 1350 | 20 | 800 | 1500 |
| 1455 | 105 | 500 | 3000 |
| 1485 | 30 | 500 | 3000 |
| 1560 | 75 | 800 | 1500 |
| Modulation Cycle 11 | | | |
| 1580 | 20 | 800 | 1500 |
| 1650 | 70 | 600 | 2500 |
| 1670 | 20 | 600 | 2500 |
| 1700 | 30 | 800 | 1500 |
| Modulation Cycle 12 | | | |
| 1720 | 20 | 800 | 1500 |
| 1740 | 20 | 700 | 2000 |
| 1760 | 20 | 700 | 2000 |
| 1780 | 20 | 800 | 1500 |
| 1800 | 20 | 800 | 1500 |

TABLE 4

Session 4 (800)

| Time (s) | Duration (s) | Low-Frequency Limit (Hz) | High-Frequency Limit (Hz) |
|---|---|---|---|
| Modulation Cycle 1 | | | |
| 0 | 20 | 800 | 1500 |
| 20 | 20 | 800 | 1500 |
| 40 | 20 | 700 | 2000 |
| 60 | 20 | 700 | 2000 |
| 80 | 20 | 800 | 1500 |
| Modulation Cycle 2 | | | |
| 100 | 20 | 800 | 1500 |
| 120 | 20 | 700 | 2000 |
| 140 | 20 | 700 | 2000 |
| 160 | 20 | 600 | 2500 |
| 180 | 20 | 600 | 2500 |
| 200 | 20 | 700 | 2000 |
| 220 | 20 | 700 | 2000 |
| 240 | 20 | 800 | 1500 |
| Modulation Cycle 3 | | | |
| 260 | 20 | 800 | 1500 |
| 280 | 20 | 700 | 2000 |
| 300 | 20 | 700 | 2000 |
| 320 | 20 | 600 | 2500 |
| 340 | 20 | 600 | 2500 |
| 360 | 20 | 550 | 3000 |
| 380 | 20 | 550 | 3000 |
| 395 | 15 | 600 | 2500 |
| 410 | 15 | 600 | 2500 |
| 425 | 15 | 700 | 2000 |
| 440 | 15 | 700 | 2000 |
| 455 | 15 | 800 | 1500 |
| Modulation Cycle 4 | | | |
| 475 | 20 | 800 | 1500 |
| 495 | 20 | 700 | 2000 |
| 515 | 20 | 700 | 2000 |
| 535 | 20 | 600 | 2500 |
| 555 | 20 | 600 | 2500 |
| 575 | 20 | 550 | 3000 |
| 595 | 20 | 550 | 3000 |
| 610 | 15 | 600 | 2500 |
| 625 | 15 | 600 | 2500 |
| 640 | 15 | 700 | 2000 |
| 655 | 15 | 700 | 2000 |
| 670 | 15 | 800 | 1500 |
| Modulation Cycle 5 | | | |
| 690 | 20 | 800 | 1500 |
| 715 | 25 | 700 | 2000 |
| 740 | 25 | 700 | 2000 |
| 765 | 25 | 600 | 2500 |
| 790 | 25 | 600 | 2500 |
| 815 | 25 | 550 | 3000 |
| 840 | 25 | 550 | 3000 |
| 865 | 25 | 500 | 3500 |
| 895 | 30 | 500 | 3500 |
| 910 | 15 | 550 | 3000 |
| 925 | 15 | 550 | 3000 |
| 940 | 15 | 600 | 2500 |
| 955 | 15 | 600 | 2500 |
| 970 | 15 | 700 | 2000 |
| 985 | 15 | 700 | 2000 |
| 1000 | 15 | 800 | 1500 |
| Modulation Cycle 6 | | | |
| 1020 | 20 | 800 | 1500 |
| 1080 | 60 | 600 | 2500 |
| 1100 | 20 | 600 | 2500 |
| 1120 | 20 | 550 | 3000 |
| 1150 | 30 | 550 | 3000 |
| 1165 | 15 | 600 | 2500 |
| 1180 | 15 | 600 | 2500 |
| 1195 | 15 | 700 | 2000 |
| 1210 | 15 | 700 | 2000 |
| 1225 | 15 | 800 | 1500 |
| Modulation Cycle 7 | | | |
| 1245 | 20 | 800 | 1500 |
| 1265 | 20 | 700 | 2000 |
| 1285 | 20 | 700 | 2000 |
| 1305 | 20 | 600 | 2500 |
| 1325 | 20 | 600 | 2500 |

TABLE 4-continued

Session 4 (800)

| Time (s) | Duration (s) | Low-Frequency Limit (Hz) | High-Frequency Limit (Hz) |
|---|---|---|---|
| 1345 | 20 | 550 | 3000 |
| 1375 | 30 | 550 | 3000 |
| 1390 | 15 | 600 | 2500 |
| 1405 | 15 | 600 | 2500 |
| 1435 | 30 | 800 | 1500 |
| Modulation Cycle 8 | | | |
| 1455 | 20 | 800 | 1500 |
| 1580 | 125 | 500 | 3500 |
| 1610 | 30 | 500 | 3500 |
| 1640 | 30 | 600 | 2500 |
| 1660 | 20 | 600 | 2500 |
| 1700 | 40 | 500 | 3500 |
| 1720 | 20 | 500 | 3500 |
| 1750 | 30 | 600 | 2500 |
| 1770 | 20 | 600 | 2500 |
| 1800 | 30 | 800 | 1500 |

TABLE 5

Session 5 (900)

| Start Time (s) | Duration (s) | Low-Frequency Limit (Hz) | High-Frequency Limit (Hz) |
|---|---|---|---|
| Modulation Cycle 1 | | | |
| 0 | 20 | 800 | 1500 |
| 20 | 20 | 800 | 1500 |
| 40 | 20 | 700 | 2000 |
| 60 | 20 | 700 | 2000 |
| 80 | 20 | 800 | 1500 |
| Modulation Cycle 2 | | | |
| 100 | 20 | 800 | 1500 |
| 120 | 20 | 700 | 2000 |
| 140 | 20 | 700 | 2000 |
| 160 | 20 | 600 | 2500 |
| 180 | 20 | 600 | 2500 |
| 200 | 20 | 700 | 2000 |
| 220 | 20 | 700 | 2000 |
| 240 | 20 | 800 | 1500 |
| Modulation Cycle 3 | | | |
| 260 | 20 | 800 | 1500 |
| 280 | 20 | 700 | 2000 |
| 300 | 20 | 700 | 2000 |
| 320 | 20 | 600 | 2500 |
| 340 | 20 | 600 | 2500 |
| 360 | 20 | 500 | 3000 |
| 380 | 20 | 500 | 3000 |
| 400 | 20 | 600 | 2500 |
| 420 | 20 | 600 | 2500 |
| 440 | 20 | 700 | 2000 |
| 460 | 20 | 700 | 2000 |
| 480 | 20 | 800 | 1500 |
| Modulation Cycle 4 | | | |
| 500 | 20 | 800 | 1500 |
| 520 | 20 | 700 | 2000 |
| 540 | 20 | 700 | 2000 |
| 560 | 20 | 600 | 2500 |
| 580 | 20 | 600 | 2500 |
| 600 | 20 | 500 | 3000 |
| 620 | 20 | 500 | 3000 |
| 635 | 15 | 600 | 2500 |
| 650 | 15 | 600 | 2500 |
| 665 | 15 | 700 | 2000 |
| 680 | 15 | 700 | 2000 |
| 695 | 15 | 800 | 1500 |
| Modulation Cycle 5 | | | |
| 715 | 20 | 800 | 1500 |
| 740 | 25 | 700 | 2000 |
| 765 | 25 | 700 | 2000 |
| 790 | 25 | 600 | 2500 |
| 815 | 25 | 600 | 2500 |
| 840 | 25 | 500 | 3000 |
| 865 | 25 | 500 | 3000 |
| 890 | 25 | 400 | 3500 |
| 920 | 30 | 400 | 3500 |
| 935 | 15 | 500 | 3000 |
| 950 | 15 | 500 | 3000 |
| 965 | 15 | 600 | 2500 |
| 980 | 15 | 600 | 2500 |
| 995 | 15 | 700 | 2000 |
| 1010 | 15 | 700 | 2000 |
| 1025 | 15 | 800 | 1500 |
| Modulation Cycle 6 | | | |
| 1045 | 20 | 800 | 1500 |
| 1105 | 60 | 600 | 2500 |
| 1125 | 20 | 600 | 2500 |
| 1155 | 30 | 500 | 3000 |
| 1185 | 30 | 500 | 3000 |
| 1200 | 15 | 600 | 2500 |
| 1215 | 15 | 600 | 2500 |
| 1230 | 15 | 700 | 2000 |
| 1245 | 15 | 700 | 2000 |
| 1260 | 15 | 800 | 1500 |
| Modulation Cycle 7 | | | |
| 1280 | 20 | 800 | 1500 |
| 1310 | 30 | 700 | 2000 |
| 1335 | 25 | 700 | 2000 |
| 1365 | 30 | 600 | 2500 |
| 1390 | 25 | 600 | 2500 |
| 1420 | 30 | 500 | 3000 |
| 1450 | 30 | 500 | 3000 |
| 1465 | 15 | 600 | 2500 |
| 1480 | 15 | 600 | 2500 |
| 1510 | 30 | 800 | 1500 |
| Modulation Cycle 8 | | | |
| 1530 | 20 | 800 | 1500 |
| 1590 | 60 | 600 | 2500 |
| 1610 | 20 | 600 | 2500 |
| 1670 | 60 | 400 | 3500 |
| 1700 | 30 | 400 | 3500 |
| 1730 | 30 | 600 | 2500 |
| 1750 | 20 | 600 | 2500 |
| 1780 | 30 | 800 | 1500 |
| 1800 | 20 | 800 | 1500 |

TABLE 6

Session 6 (1000)

| Start Time (s) | Duration (s) | Low-Frequency Limit (Hz) | High-Frequency Limit (Hz) |
|---|---|---|---|
| Modulation Cycle 1 | | | |
| 0 | 20 | 800 | 1500 |
| 20 | 20 | 800 | 1500 |
| 40 | 20 | 700 | 2000 |
| 60 | 20 | 700 | 2000 |
| 80 | 20 | 600 | 2500 |
| 100 | 20 | 600 | 2500 |
| 120 | 20 | 500 | 3000 |
| 140 | 20 | 500 | 3000 |
| 160 | 20 | 600 | 2500 |

TABLE 6-continued

Session 6 (1000)

| Start Time (s) | Duration (s) | Low-Frequency Limit (Hz) | High-Frequency Limit (Hz) |
|---|---|---|---|
| 180 | 20 | 600 | 2500 |
| 200 | 20 | 700 | 2000 |
| 220 | 20 | 700 | 2000 |
| 240 | 20 | 800 | 1500 |
| Modulation Cycle 2 | | | |
| 260 | 20 | 800 | 1500 |
| 280 | 20 | 700 | 2000 |
| 300 | 20 | 700 | 2000 |
| 320 | 20 | 600 | 2500 |
| 340 | 20 | 600 | 2500 |
| 360 | 20 | 500 | 3000 |
| 380 | 20 | 500 | 3000 |
| 400 | 20 | 400 | 3500 |
| 420 | 20 | 400 | 3500 |
| 440 | 20 | 500 | 3000 |
| 460 | 20 | 500 | 3000 |
| 480 | 20 | 600 | 2500 |
| 500 | 20 | 600 | 2500 |
| 520 | 20 | 700 | 2000 |
| 540 | 20 | 700 | 2000 |
| 560 | 20 | 800 | 1500 |
| Modulation Cycle 3 | | | |
| 580 | 20 | 800 | 1500 |
| 605 | 25 | 700 | 2000 |
| 630 | 25 | 700 | 2000 |
| 655 | 25 | 600 | 2500 |
| 680 | 25 | 600 | 2500 |
| 705 | 25 | 500 | 3000 |
| 730 | 25 | 500 | 3000 |
| 755 | 25 | 450 | 3500 |
| 780 | 25 | 450 | 3500 |
| 805 | 25 | 400 | 4000 |
| 825 | 20 | 400 | 4000 |
| 840 | 15 | 450 | 3500 |
| 855 | 15 | 450 | 3500 |
| 870 | 15 | 500 | 3000 |
| 885 | 15 | 500 | 3000 |
| 900 | 15 | 600 | 2500 |
| 915 | 15 | 600 | 2500 |
| 930 | 15 | 700 | 2000 |
| 945 | 15 | 700 | 2000 |
| 960 | 15 | 800 | 1500 |
| Modulation Cycle 4 | | | |
| 980 | 20 | 800 | 1500 |
| 1005 | 25 | 700 | 2000 |
| 1030 | 25 | 700 | 2000 |
| 1055 | 25 | 600 | 2500 |
| 1080 | 25 | 600 | 2500 |
| 1105 | 25 | 500 | 3000 |
| 1130 | 25 | 500 | 3000 |
| 1155 | 25 | 450 | 3500 |
| 1180 | 25 | 450 | 3500 |
| 1205 | 25 | 400 | 4000 |
| 1230 | 25 | 400 | 4000 |
| 1245 | 15 | 450 | 3500 |
| 1260 | 15 | 450 | 3500 |
| 1275 | 15 | 500 | 3000 |
| 1290 | 15 | 500 | 3000 |
| 1305 | 15 | 600 | 2500 |
| 1325 | 20 | 600 | 2500 |
| 1385 | 60 | 400 | 3500 |
| 1415 | 30 | 400 | 3500 |
| 1445 | 30 | 600 | 2500 |
| 1460 | 15 | 600 | 2500 |
| 1490 | 30 | 800 | 1500 |
| Modulation Cycle 5 | | | |
| 1510 | 20 | 800 | 1500 |
| 1600 | 90 | 500 | 3000 |
| 1620 | 20 | 500 | 3000 |
| 1680 | 60 | 400 | 4000 |
| 1710 | 30 | 400 | 4000 |
| 1740 | 30 | 500 | 3000 |
| 1755 | 15 | 500 | 3000 |
| 1800 | 45 | 800 | 1500 |

TABLE 7

Session 7 (1100)

| Start Time (s) | Duration (s) | Low-Frequency Limit (Hz) | High-Frequency Limit (Hz) |
|---|---|---|---|
| Modulation Cycle 1 | | | |
| 0 | 20 | 800 | 1500 |
| 20 | 20 | 800 | 1500 |
| 40 | 20 | 700 | 2000 |
| 60 | 20 | 700 | 2000 |
| 80 | 20 | 600 | 2500 |
| 100 | 20 | 600 | 2500 |
| 120 | 20 | 500 | 3000 |
| 140 | 20 | 500 | 3000 |
| 160 | 20 | 600 | 2500 |
| 180 | 20 | 600 | 2500 |
| 200 | 20 | 700 | 2000 |
| 220 | 20 | 700 | 2000 |
| 240 | 20 | 800 | 1500 |
| Modulation Cycle 2 | | | |
| 260 | 20 | 800 | 1500 |
| 280 | 20 | 700 | 2000 |
| 300 | 20 | 700 | 2000 |
| 320 | 20 | 600 | 2500 |
| 340 | 20 | 600 | 2500 |
| 360 | 20 | 500 | 3000 |
| 380 | 20 | 500 | 3000 |
| 400 | 20 | 400 | 3500 |
| 420 | 20 | 400 | 3500 |
| 440 | 20 | 500 | 3000 |
| 460 | 20 | 500 | 3000 |
| 480 | 20 | 600 | 2500 |
| 500 | 20 | 600 | 2500 |
| 520 | 20 | 700 | 2000 |
| 540 | 20 | 700 | 2000 |
| 560 | 20 | 800 | 1500 |
| Modulation Cycle 3 | | | |
| 580 | 20 | 800 | 1500 |
| 605 | 25 | 700 | 2000 |
| 630 | 25 | 700 | 2000 |
| 655 | 25 | 600 | 2500 |
| 680 | 25 | 600 | 2500 |
| 705 | 25 | 500 | 3000 |
| 730 | 25 | 500 | 3000 |
| 755 | 25 | 400 | 3500 |
| 780 | 25 | 400 | 3500 |
| 805 | 25 | 300 | 4000 |
| 825 | 20 | 300 | 4000 |
| 840 | 15 | 400 | 3500 |
| 855 | 15 | 400 | 3500 |
| 870 | 15 | 500 | 3000 |
| 885 | 15 | 500 | 3000 |
| 900 | 15 | 600 | 2500 |
| 915 | 15 | 600 | 2500 |
| 930 | 15 | 700 | 2000 |
| 945 | 15 | 700 | 2000 |
| 960 | 15 | 800 | 1500 |
| Modulation Cycle 4 | | | |
| 980 | 20 | 800 | 1500 |
| 1005 | 25 | 700 | 2000 |
| 1030 | 25 | 700 | 2000 |
| 1055 | 25 | 600 | 2500 |

TABLE 7-continued

Session 7 (1100)

| Start Time (s) | Duration (s) | Low-Frequency Limit (Hz) | High-Frequency Limit (Hz) |
|---|---|---|---|
| 1080 | 25 | 600 | 2500 |
| 1105 | 25 | 500 | 3000 |
| 1130 | 25 | 500 | 3000 |
| 1155 | 25 | 400 | 3500 |
| 1180 | 25 | 400 | 3500 |
| 1205 | 25 | 300 | 4000 |
| 1230 | 25 | 300 | 4000 |
| 1245 | 15 | 400 | 3500 |
| 1260 | 15 | 400 | 3500 |
| 1275 | 15 | 500 | 3000 |
| 1290 | 15 | 500 | 3000 |
| 1305 | 15 | 600 | 2500 |
| 1325 | 20 | 600 | 2500 |
| 1385 | 60 | 400 | 3500 |
| 1415 | 30 | 400 | 3500 |
| 1445 | 30 | 600 | 2500 |
| 1460 | 15 | 600 | 2500 |
| 1490 | 30 | 800 | 1500 |
| Modulation Cycle 5 | | | |
| 1510 | 20 | 800 | 1500 |
| 1600 | 90 | 500 | 3000 |
| 1620 | 20 | 500 | 3000 |
| 1680 | 60 | 300 | 4000 |
| 1710 | 30 | 300 | 4000 |
| 1740 | 30 | 500 | 3000 |
| 1755 | 15 | 500 | 3000 |
| 1800 | 45 | 800 | 1500 |

TABLE 8

Sessions 8 and 9 (1200)

| Start Time (s) | Duration (s) | Low-Frequency Limit (Hz) | High-Frequency Limit (Hz) |
|---|---|---|---|
| Modulation Cycle 1 | | | |
| 0 | 20 | 800 | 1500 |
| 20 | 20 | 800 | 1500 |
| 40 | 20 | 700 | 2000 |
| 60 | 20 | 700 | 2000 |
| 80 | 20 | 600 | 2500 |
| 100 | 20 | 600 | 2500 |
| 120 | 20 | 500 | 3000 |
| 140 | 20 | 500 | 3000 |
| 160 | 20 | 600 | 2500 |
| 180 | 20 | 600 | 2500 |
| 200 | 20 | 700 | 2000 |
| 220 | 20 | 700 | 2000 |
| 240 | 20 | 800 | 1500 |
| Modulation Cycle 2 | | | |
| 260 | 20 | 800 | 1500 |
| 280 | 20 | 700 | 2000 |
| 300 | 20 | 700 | 2000 |
| 320 | 20 | 600 | 2500 |
| 340 | 20 | 600 | 2500 |
| 360 | 20 | 500 | 3000 |
| 380 | 20 | 500 | 3000 |
| 400 | 20 | 400 | 3500 |
| 420 | 20 | 400 | 3500 |
| 440 | 20 | 500 | 3000 |
| 460 | 20 | 500 | 3000 |
| 480 | 20 | 600 | 2500 |
| 500 | 20 | 600 | 2500 |
| 520 | 20 | 700 | 2000 |
| 540 | 20 | 700 | 2000 |
| 560 | 20 | 800 | 1500 |

TABLE 8-continued

Sessions 8 and 9 (1200)

| Start Time (s) | Duration (s) | Low-Frequency Limit (Hz) | High-Frequency Limit (Hz) |
|---|---|---|---|
| Modulation Cycle 3 | | | |
| 580 | 20 | 800 | 1500 |
| 640 | 60 | 600 | 2500 |
| 660 | 20 | 600 | 2500 |
| 680 | 20 | 500 | 3000 |
| 700 | 20 | 500 | 3000 |
| 720 | 20 | 400 | 3500 |
| 740 | 20 | 400 | 3500 |
| 760 | 20 | 300 | 4000 |
| 780 | 20 | 300 | 4000 |
| 800 | 20 | 400 | 3500 |
| 820 | 20 | 400 | 3500 |
| 840 | 20 | 500 | 3000 |
| 860 | 20 | 500 | 3000 |
| 880 | 20 | 600 | 2500 |
| 900 | 20 | 600 | 2500 |
| 960 | 60 | 800 | 1500 |
| Modulation Cycle 4 | | | |
| 980 | 20 | 800 | 1500 |
| 1080 | 100 | 500 | 3000 |
| 1100 | 20 | 500 | 3000 |
| 1120 | 20 | 400 | 3500 |
| 1140 | 20 | 400 | 3500 |
| 1160 | 20 | 300 | 4000 |
| 1180 | 20 | 300 | 4000 |
| 1200 | 20 | 200 | 4500 |
| 1220 | 20 | 200 | 4500 |
| 1240 | 20 | 300 | 4000 |
| 1260 | 20 | 300 | 4000 |
| 1280 | 20 | 400 | 3500 |
| 1300 | 20 | 400 | 3500 |
| 1320 | 20 | 500 | 3000 |
| 1340 | 20 | 500 | 3000 |
| 1405 | 65 | 800 | 1500 |
| Modulation Cycle 5 | | | |
| 1425 | 20 | 800 | 1500 |
| 1515 | 90 | 500 | 3000 |
| 1535 | 20 | 500 | 3000 |
| 1575 | 40 | 300 | 4000 |
| 1595 | 20 | 300 | 4000 |
| 1615 | 20 | 200 | 4500 |
| 1645 | 30 | 200 | 4500 |
| 1665 | 20 | 300 | 4000 |
| 1685 | 20 | 300 | 4000 |
| 1725 | 40 | 500 | 3000 |
| 1745 | 20 | 500 | 3000 |
| 1800 | 55 | 800 | 1500 |

TABLE 9

Session 10 (1300)

| Start Time (s) | Duration (s) | Low-Frequency Limit (Hz) | High-Frequency Limit (Hz) |
|---|---|---|---|
| Modulation Cycle 1 | | | |
| 0 | 20 | 800 | 1500 |
| 20 | 20 | 800 | 1500 |
| 40 | 20 | 700 | 2000 |
| 60 | 20 | 700 | 2000 |
| 80 | 20 | 600 | 2500 |
| 100 | 20 | 600 | 2500 |
| 120 | 20 | 500 | 3000 |
| 140 | 20 | 500 | 3000 |
| 160 | 20 | 400 | 3500 |
| 180 | 20 | 400 | 3500 |
| 195 | 15 | 500 | 3000 |
| 210 | 15 | 500 | 3000 |

TABLE 9-continued

Session 10 (1300)

| Start Time (s) | Duration (s) | Low-Frequency Limit (Hz) | High-Frequency Limit (Hz) |
|---|---|---|---|
| 225 | 15 | 600 | 2500 |
| 240 | 15 | 600 | 2500 |
| 255 | 15 | 700 | 2000 |
| Modulation Cycle 2 | | | |
| 275 | 20 | 700 | 2000 |
| 295 | 20 | 600 | 2500 |
| 315 | 20 | 600 | 2500 |
| 335 | 20 | 500 | 3000 |
| 355 | 20 | 500 | 3000 |
| 375 | 20 | 400 | 3500 |
| 395 | 20 | 400 | 3500 |
| 415 | 20 | 300 | 4000 |
| 435 | 20 | 300 | 4000 |
| 450 | 15 | 400 | 3500 |
| 465 | 15 | 400 | 3500 |
| 480 | 15 | 500 | 3000 |
| 495 | 15 | 500 | 3000 |
| 510 | 15 | 600 | 2500 |
| 525 | 15 | 600 | 2500 |
| 540 | 15 | 700 | 2000 |
| 555 | 15 | 700 | 2000 |
| 575 | 20 | 800 | 1500 |
| Modulation Cycle 3 | | | |
| 595 | 20 | 800 | 1500 |
| 615 | 20 | 700 | 2000 |
| 635 | 20 | 700 | 2000 |
| 655 | 20 | 600 | 2500 |
| 675 | 20 | 600 | 2500 |
| 695 | 20 | 500 | 3000 |
| 715 | 20 | 500 | 3000 |
| 735 | 20 | 400 | 3500 |
| 755 | 20 | 400 | 3500 |
| 775 | 20 | 300 | 4000 |
| 795 | 20 | 300 | 4000 |
| 815 | 20 | 250 | 4500 |
| 835 | 20 | 250 | 4500 |
| 850 | 15 | 300 | 4000 |
| 865 | 15 | 300 | 4000 |
| 895 | 30 | 500 | 3000 |
| 910 | 15 | 500 | 3000 |
| 955 | 45 | 800 | 1500 |
| Modulation Cycle 4 | | | |
| 975 | 20 | 800 | 1500 |
| 1065 | 90 | 500 | 3000 |
| 1085 | 20 | 500 | 3000 |
| 1175 | 90 | 250 | 4500 |
| 1195 | 20 | 250 | 4500 |
| 1215 | 20 | 200 | 5000 |
| 1245 | 30 | 200 | 5000 |
| 1260 | 15 | 250 | 4500 |
| 1275 | 15 | 250 | 4500 |
| 1320 | 45 | 500 | 3000 |
| 1335 | 15 | 500 | 3000 |
| 1365 | 30 | 700 | 2000 |
| Modulation Cycle 5 | | | |
| 1385 | 20 | 700 | 2000 |
| 1475 | 90 | 400 | 3500 |
| 1495 | 20 | 400 | 3500 |
| 1585 | 90 | 200 | 5000 |
| 1615 | 30 | 200 | 5000 |
| 1680 | 65 | 400 | 3500 |
| 1700 | 20 | 400 | 3500 |
| 1780 | 80 | 800 | 1500 |
| 1800 | 20 | 800 | 1500 |

TABLE 10

Booster 1 (1400)

| Start Time (s) | Duration (s) | Low-Frequency Limit (Hz) | High-Frequency Limit (Hz) |
|---|---|---|---|
| 0 | 20 | 800 | 1500 |
| 20 | 20 | 800 | 1500 |
| 40 | 20 | 700 | 2000 |
| 60 | 20 | 700 | 2000 |
| 80 | 20 | 600 | 2500 |
| 100 | 20 | 600 | 2500 |
| 120 | 20 | 500 | 3000 |
| 140 | 20 | 500 | 3000 |
| 160 | 20 | 400 | 3500 |
| 180 | 20 | 400 | 3500 |
| 195 | 15 | 500 | 3000 |
| 210 | 15 | 500 | 3000 |
| 225 | 15 | 600 | 2500 |
| 240 | 15 | 600 | 2500 |
| 255 | 15 | 700 | 2000 |
| 275 | 20 | 700 | 2000 |
| 295 | 20 | 600 | 2500 |
| 315 | 20 | 600 | 2500 |
| 335 | 20 | 500 | 3000 |
| 355 | 20 | 500 | 3000 |
| 375 | 20 | 400 | 3500 |
| 395 | 20 | 400 | 3500 |
| 415 | 20 | 300 | 4000 |
| 435 | 20 | 300 | 4000 |
| 450 | 15 | 400 | 3500 |
| 465 | 15 | 400 | 3500 |
| 480 | 15 | 500 | 3000 |
| 495 | 15 | 500 | 3000 |
| 510 | 15 | 600 | 2500 |
| 525 | 15 | 600 | 2500 |
| 540 | 15 | 700 | 2000 |
| 555 | 15 | 700 | 2000 |
| 575 | 20 | 800 | 1500 |
| 600 | 25 | 800 | 1500 |

TABLE 11

Booster 2 (1500)

| Start Time (s) | Duration (s) | Low-Frequency Limit (Hz) | High-Frequency Limit (Hz) |
|---|---|---|---|
| 0 | 15 | 800 | 1500 |
| 15 | 15 | 700 | 2000 |
| 35 | 20 | 700 | 2000 |
| 55 | 20 | 600 | 2500 |
| 75 | 20 | 600 | 2500 |
| 95 | 20 | 500 | 3000 |
| 115 | 20 | 500 | 3000 |
| 135 | 20 | 400 | 3500 |
| 155 | 20 | 400 | 3500 |
| 175 | 20 | 300 | 4000 |
| 195 | 20 | 300 | 4000 |
| 215 | 20 | 250 | 4500 |
| 235 | 20 | 250 | 4500 |
| 250 | 15 | 300 | 4000 |
| 265 | 15 | 300 | 4000 |
| 295 | 30 | 500 | 3000 |
| 310 | 15 | 500 | 3000 |
| 355 | 45 | 800 | 1500 |
| 375 | 20 | 800 | 1500 |
| 465 | 90 | 500 | 3000 |
| 485 | 20 | 500 | 3000 |
| 575 | 90 | 250 | 4500 |
| 600 | 25 | 250 | 4500 |

TABLE 12

| Booster 3 (1600) | | | |
|---|---|---|---|
| Start Time (s) | Duration (s) | Low-Frequency Limit (Hz) | High-Frequency Limit (Hz) |
| 0 | 30 | 200 | 5000 |
| 30 | 30 | 200 | 5000 |
| 45 | 15 | 300 | 4500 |
| 60 | 15 | 300 | 4500 |
| 105 | 45 | 500 | 3000 |
| 120 | 15 | 500 | 3000 |
| 150 | 30 | 800 | 2000 |
| 170 | 20 | 800 | 2000 |
| 260 | 90 | 400 | 3500 |
| 280 | 20 | 400 | 3500 |
| 370 | 90 | 200 | 5000 |
| 400 | 30 | 200 | 5000 |
| 465 | 65 | 400 | 3500 |
| 485 | 20 | 400 | 3500 |
| 565 | 80 | 800 | 1500 |
| 600 | 35 | 800 | 1500 |

What is claimed is:

1. A method comprising:
processing an acoustic input signal to produce acoustic stimuli during a session, wherein the processing is based on processing parameters comprising:
  a first frequency modulation cycle comprising:
    a first initial modulation comprising:
      a first initial low-frequency limit; and
      a first initial high-frequency limit;
    a first widest modulation comprising:
      a first minimum low-frequency limit; and
      a first maximum high-frequency limit,
      wherein the first minimum low-frequency limit is lower than the first initial low frequency limit and/or the first maximum high-frequency limit is higher than the first initial high frequency limit; and
    a first final modulation comprising:
      a first final low-frequency limit that is substantially similar to the first initial low-frequency limit; and
      a first final high-frequency limit that is substantially similar to the first initial high-frequency limit; and
  a second frequency modulation cycle comprising:
    a second initial modulation comprising:
      a second initial low-frequency limit; and
      a second initial high-frequency limit;
    a second widest modulation comprising:
      a second minimum low-frequency limit; and
      a second maximum high-frequency limit,
      wherein the second minimum low-frequency limit is lower than the second initial lower frequency limit and/or the second maximum high-frequency limit is higher than the second initial high frequency limit; and
    a second final modulation comprising:
      a second final low-frequency limit that is substantially similar to the second initial low-frequency limit; and
      a second final high-frequency limit that is substantially similar to the second initial high-frequency limit,
wherein the second minimum low-frequency limit is lower than the first minimum low-frequency limit and/or the second maximum high-frequency limit is higher than the first maximum high-frequency limit;
transmitting the acoustic stimuli to the subject during the session.

2. A method according to claim 1, further comprising:
measuring one or more characteristics of the subject before processing the acoustic input signal to acoustic stimuli,
wherein the one more characteristics are selected from the group consisting of: sound sensitivity, behavioral state regulation, autonomic state regulation, auditory processing, one or more social engagement skills, sucking, swallowing, breathing, one or more acoustic properties of vocalization of the subject, HRV, RSA, heart rate, blood pressure, cognitive ability, pain level, anxiety level, blood sugar level, usage of one or more facial muscles, usage of one or more head-turning muscles and a middle-ear transfer function.

3. A method according to claim 2, wherein:
the one or more characteristics comprises the middle-ear transfer function, and
the measuring comprises using a middle-ear sound absorption ("MESA") system.

4. A method according to claim 2, further comprising adjusting one or more of the processing parameters based on the one or more measured characteristics.

5. A method according to claim 2, further comprising:
determining an updated measurement of the one or more measured characteristics during or after the transmitting the acoustic stimuli to the subject; and,
determining that the subject has experienced a user response, based on the updated measurement, the user response comprising one or more of: reduced sound sensitivity, improved auditory processing, improved behavioral state regulation, improved autonomic state regulation, and improved social engagement.

6. A method according to claim 1, further comprising:
processing a second acoustic input signal, based on the processing parameters, to produce second acoustic stimuli during the session; and
transmitting the second acoustic stimuli to only a first ear of the subject during the session,
wherein the first acoustic stimuli is transmitted to only a second ear of the subject during the session.

7. A method according to claim 6, wherein:
the first acoustic input signal comprises human vocalization; and
the second acoustic input signal does not comprise human vocalization.

8. A method according to claim 1, wherein the acoustic input signal comprises one or more of human speech, human singing, instrumental music and synthesized music.

9. A method according to claim 8, wherein the acoustic input signal is selected from the group consisting of animated movie soundtracks, lullabies, love songs, folk songs and bluegrass ballads.

10. A method according to claim 8, wherein the acoustic input signal comprises melodic voices above about 261.6 Hz and a varying volume level.

11. A method according to claim 1, wherein the first and second frequency modulation cycles are seamlessly connected in time.

12. A method according to claim 1, wherein:
the second initial low-frequency limit is substantially similar to the first initial low-frequency limit, and
the second initial high-frequency limit is substantially similar to the first initial high-frequency limit.

13. A method according to claim 1, wherein:
the first initial low-frequency limit is from about 600 Hz to about 900 Hz, and
the first initial high-frequency limit is from about 1,400 Hz to about 2,000 Hz.

14. A method according to claim 1, wherein:
each of the first and second minimum low-frequency limits comprises a frequency of from about 300 Hz to about 1,000 Hz, and
each of the first and second maximum high-frequency limits comprises a frequency of from about 1,500 Hz to about 5,000 Hz.

15. A method according to claim 1, further comprising:
displaying visual stimuli to the subject during the first session,
wherein the visual stimuli and the acoustic stimuli are synchronized.

16. A method according to claim 15, wherein the visual stimuli comprises a virtual reality environment.

17. A system comprising:
a measurement device adapted to measure one or more characteristics relating to a subject, the one more characteristics selected from the group consisting of: sound sensitivity, behavioral state regulation, autonomic state regulation, auditory processing, one or more social engagement skills, sucking, swallowing, breathing, one or more acoustic properties of vocalization of the subject, HRV, RSA, heart rate, blood pressure, cognitive ability, pain level, anxiety level, blood sugar level, usage of one or more facial muscles, usage of one or more head-turning muscles and a middle-ear transfer function;
an audio processing device in communication with the measurement device, the audio processing device adapted to:
determine processing parameters based on the measured characteristics, the processing parameters comprising:
a first frequency modulation cycle comprising:
a first initial modulation comprising a first initial low-frequency limit and a first initial high-frequency limit;
a first widest modulation comprising a first minimum low-frequency limit and a first maximum high-frequency limit,
wherein the first minimum low-frequency limit is lower than the first initial low frequency limit and/or the first maximum high-frequency limit is higher than the first initial high frequency limit; and
a first final modulation comprising:
a first final low-frequency limit that is substantially similar to the first initial low-frequency limit; and
a first final high-frequency limit that is substantially similar to the first initial high-frequency limit; and
a second frequency modulation cycle comprising:
a second initial modulation comprising a second initial low-frequency limit and a second initial high-frequency limit;
a second widest modulation comprising a second minimum low-frequency limit and a second maximum high-frequency limit,
wherein the second minimum low-frequency limit is lower than the second initial lower frequency limit and/or the second maximum high-frequency limit is higher than the second initial high frequency limit; and
a second final modulation comprising:
a second final low-frequency limit that is substantially similar to the second initial low-frequency limit; and
a second final high-frequency limit that is substantially similar to the second initial high-frequency limit,
wherein the second minimum low-frequency limit is lower than the first minimum low-frequency limit and/or the second maximum high-frequency limit is higher than the first maximum high-frequency limit;
process an acoustic input signal according to the processing parameters to generate acoustic stimuli; and
transmit the acoustic stimuli to the subject.

18. A system according to claim 17, further comprising a listening device in communication with the audio processing device, the listening device adapted to:
receive the acoustic stimuli from the audio processing device; and
output the acoustic stimuli to the subject.

19. An apparatus comprising:
one or more sensors adapted to measure one or more characteristics relating to a subject, the one more characteristics selected from the group consisting of: sound sensitivity, behavioral state regulation, autonomic state regulation, auditory processing, one or more social engagement skills, sucking, swallowing, breathing, one or more acoustic properties of vocalization of the subject, HRV, RSA, heart rate, blood pressure, cognitive ability, pain level, anxiety level, blood sugar level, usage of one or more facial muscles, usage of one or more head-turning muscles and a middle-ear transfer function;
an audio processor adapted to:
determine processing parameters based on the measured characteristics, the processing parameters comprising:
a first frequency modulation cycle comprising:
a first initial modulation comprising a first initial low-frequency limit and a first initial high-frequency limit;
a first widest modulation comprising a first minimum low-frequency limit and a first maximum high-frequency limit,
wherein the first minimum low-frequency limit is lower than the first initial low frequency limit and/or the first maximum high-frequency limit is higher than the first initial high frequency limit; and
a first final modulation comprising:
a first final low-frequency limit that is substantially similar to the first initial low-frequency limit; and
a first final high-frequency limit that is substantially similar to the first initial high-frequency limit; and
a second frequency modulation cycle comprising:
a second initial modulation comprising a second initial low-frequency limit and a second initial high-frequency limit;
a second widest modulation comprising a second minimum low-frequency limit and a second maximum high-frequency limit, wherein the second minimum low-frequency limit is lower than the second initial lower frequency limit and/or the second maximum high-frequency limit is higher than the second initial high frequency limit; and
a second final modulation comprising:
a second final low-frequency limit that is substantially similar to the second initial low-frequency limit; and
a second final high-frequency limit that is substantially similar to the second initial high-frequency limit,
wherein the second minimum low-frequency limit is lower than the first minimum low-frequency limit and/or the second maximum high-frequency limit is higher than the first maximum high-frequency limit;
process an acoustic input signal according to the processing parameters to generate acoustic stimuli; and
an output transducer adapted to transmit the acoustic stimuli to the subject.

\* \* \* \* \*